United States Patent
LeBowitz

(10) Patent No.: US 7,981,864 B2
(45) Date of Patent: Jul. 19, 2011

(54) METHODS AND COMPOSITIONS FOR TARGETING PROTEINS ACROSS THE BLOOD BRAIN BARRIER

(75) Inventor: Jonathan LeBowitz, Frontenac, MO (US)

(73) Assignee: Biomarin Pharmaceutical Inc., Novato, CA (US)

( * ) Notice: Subject to any disclaimer, the term of this patent is extended or adjusted under 35 U.S.C. 154(b) by 90 days.

(21) Appl. No.: 12/033,802

(22) Filed: Feb. 19, 2008

(65) Prior Publication Data

US 2008/0241118 A1 Oct. 2, 2008

Related U.S. Application Data

(63) Continuation of application No. 11/234,876, filed on Sep. 23, 2005, now abandoned, which is a continuation of application No. 10/136,639, filed on Apr. 30, 2002, now abandoned.

(60) Provisional application No. 60/329,650, filed on Oct. 16, 2001.

(51) Int. Cl.
*A61K 38/30* (2006.01)
*A61K 38/00* (2006.01)
*A61K 38/43* (2006.01)
*C07K 14/65* (2006.01)

(52) U.S. Cl. ........... 514/8.6; 514/1.1; 514/8.5; 530/399; 424/94.1

(58) Field of Classification Search ................ None
See application file for complete search history.

(56) References Cited

U.S. PATENT DOCUMENTS

| | | | |
|---|---|---|---|
| 4,309,776 A | 1/1982 | Berguer | |
| 4,522,811 A | 6/1985 | Eppstein et al. | |
| 4,749,570 A | 6/1988 | Poznansky | |
| 4,801,575 A | 1/1989 | Pardridge | |
| 4,902,505 A | 2/1990 | Pardridge et al. | |
| 5,126,324 A * | 6/1992 | Clark et al. | 514/12 |
| 5,236,838 A | 8/1993 | Rasmussen et al. | |
| 5,258,453 A | 11/1993 | Kopecek et al. | |
| 5,356,804 A | 10/1994 | Desnick et al. | |
| 5,399,346 A | 3/1995 | Anderson et al. | |
| 5,405,942 A | 4/1995 | Bell et al. | |
| 5,470,828 A | 11/1995 | Ballard et al. | |
| 5,476,779 A | 12/1995 | Chen et al. | |
| 5,549,892 A | 8/1996 | Friedman et al. | |

(Continued)

FOREIGN PATENT DOCUMENTS

EP 0196056 A2 10/1986

(Continued)

OTHER PUBLICATIONS

Bagley et al. Biochem J. May 1, 1989; 259(3): 665-671.*

(Continued)

*Primary Examiner* — David S Romeo
*Assistant Examiner* — Daniel C Gamett
(74) *Attorney, Agent, or Firm* — Marshall, Gerstein & Borun

(57) ABSTRACT

Disclosed are methods and compositions for targeting therapeutic proteins to the brain. Methods and compositions of the invention involve associating an IGF moiety with a therapeutic protein in order to target the therapeutic protein to the brain. Soluble fusion proteins that include an IGF targeting moiety are transported to neural tissue in the brain from blood. Methods and compositions of the invention include therapeutic applications for treating lysosomal storage diseases. The invention also provides nucleic acids and cells for expressing IGF fusion proteins.

8 Claims, 9 Drawing Sheets

Alignment of human IGF-I and IGF-II mature proteins showing location of domains.

U.S. PATENT DOCUMENTS

| | | | |
|---|---|---|---|
| 5,580,757 A | 12/1996 | Desnick et al. |
| 5,633,234 A | 5/1997 | August et al. |
| 5,633,235 A | 5/1997 | Townsend et al. |
| 5,704,910 A | 1/1998 | Humes |
| 5,736,363 A | 4/1998 | Edwards et al. |
| 5,798,366 A | 8/1998 | Platt et al. |
| 5,817,623 A | 10/1998 | Ishii |
| 5,817,789 A | 10/1998 | Heartlein et al. |
| 5,827,703 A | 10/1998 | Debs et al. |
| 5,854,025 A | 12/1998 | Edwards et al. |
| 5,977,307 A | 11/1999 | Friden et al. |
| 5,981,194 A | 11/1999 | Jefferies et al. |
| 6,020,144 A | 2/2000 | Gueiros-Filho et al. |
| 6,027,921 A | 2/2000 | Heartlein et al. |
| 6,066,626 A | 5/2000 | Yew et al. |
| 6,083,725 A | 7/2000 | Selden et al. |
| 6,118,045 A | 9/2000 | Reuser et al. |
| 6,226,603 B1 | 5/2001 | Freire et al. |
| 6,235,874 B1 | 5/2001 | Wu et al. |
| 6,262,026 B1 | 7/2001 | Heartlein et al. |
| 6,270,989 B1 | 8/2001 | Treco et al. |
| 6,273,598 B1 | 8/2001 | Keck et al. |
| 6,281,010 B1 | 8/2001 | Gao et al. |
| 6,284,875 B1 | 9/2001 | Turpen et al. |
| 6,329,501 B1 | 12/2001 | Smith et al. |
| 6,344,436 B1 | 2/2002 | Smith et al. |
| 6,348,194 B1 | 2/2002 | Huse et al. |
| 6,441,147 B1 | 8/2002 | Turpen et al. |
| 6,451,600 B1 | 9/2002 | Rasmussen et al. |
| 6,455,494 B1 | 9/2002 | Jefferies et al. |
| 6,472,140 B1 | 10/2002 | Tanzi et al. |
| 6,537,785 B1 | 3/2003 | Canfield |
| 6,566,099 B1 | 5/2003 | Selden et al. |
| 6,569,661 B1 | 5/2003 | Qin et al. |
| 6,596,500 B1 | 7/2003 | Kang et al. |
| 7,396,811 B2 | 7/2008 | LeBowitz et al. |
| 2001/0006635 A1 | 7/2001 | Bennett et al. |
| 2001/0025026 A1 | 9/2001 | Heartlein et al. |
| 2002/0013953 A1 | 1/2002 | Reuser et al. |
| 2002/0081654 A1 | 6/2002 | Sandrin et al. |
| 2002/0110551 A1 | 8/2002 | Chen |
| 2002/0142299 A1 | 10/2002 | Davidson et al. |
| 2003/0004236 A1 | 1/2003 | Meade |
| 2003/0021787 A1 | 1/2003 | Hung et al. |
| 2003/0077806 A1 | 4/2003 | Selden et al. |
| 2003/0082176 A1 | 5/2003 | LeBowitz et al. |
| 2004/0005309 A1 | 1/2004 | LeBowitz et al. |
| 2004/0006008 A1 | 1/2004 | LeBowitz et al. |
| 2004/0029779 A1 | 2/2004 | Zhu et al. |
| 2004/0081645 A1 | 4/2004 | Van Bree et al. |
| 2004/0248262 A1 | 12/2004 | Koeberl et al. |
| 2005/0026823 A1 | 2/2005 | Zankel et al. |
| 2005/0058634 A1 | 3/2005 | Zhu |
| 2005/0281805 A1 | 12/2005 | LeBowitz et al. |

FOREIGN PATENT DOCUMENTS

| | | |
|---|---|---|
| EP | 0466222 A1 | 1/1992 |
| EP | 0599303 A2 | 6/1994 |
| WO | WO-9104014 A1 | 4/1991 |
| WO | WO-9114438 A1 | 10/1991 |
| WO | WO-9222332 A2 | 12/1992 |
| WO | WO-9306216 A1 | 4/1993 |
| WO | WO-9310819 A1 | 6/1993 |
| WO | WO-9402178 A1 | 2/1994 |
| WO | WO-9502421 A1 | 1/1995 |
| WO | WO-0053730 A2 | 9/2000 |
| WO | WO-0119955 A2 | 3/2001 |
| WO | WO-0153730 A1 | 7/2001 |
| WO | WO-0244355 A2 | 6/2002 |
| WO | WO-02056907 A2 | 7/2002 |
| WO | WO-02087510 A2 | 11/2002 |
| WO | WO-03032727 A1 | 4/2003 |
| WO | WO-03032913 A2 | 4/2003 |
| WO | WO-03057179 A2 | 7/2003 |
| WO | WO-03102583 A1 | 12/2003 |
| WO | WO-2005078077 A2 | 8/2005 |

OTHER PUBLICATIONS

"Purification," The QIAexpressionist, pp. 63-107 (2001).

"QIAexpress Protein Purification System"QIAexpress—The Complete System for 6xHis Technology pp. 7-12, (2001).

Achord et al., "Human β-Glucuronidase. II. Fate of Infused Human Placental β-Glucuronidase in the Rat," Pediat. Res., 11:816-822 (1977).

Achord, et al., "Human β-Glucuronidase: In Vivo Clearance and in Vitro Uptake by a Glycoprotein Recognition System on Reticuloendothelial Cells" Cell, 15:269-278 (1978).

Aeed and Elhammer, "Glycosylation of recombinant prorenin in insect cells: the insect cell line Sf9 does not express the mannose 6-phosphate recognition signal. Glycosylation of recombinant prorenin in insect cells: the insect cell line Sf9 does not express the mannose", Biochemistry, 33(29):8793-0797 (1994).

Aerts et al., "Efficient Routing of Glucocerebrosidase to Lysosomes Requires Complex Oligosaccharide Chain Formation," Biochem. Biophys. Res. Commun., 141(2):452-458 (1986).

Allen et al., "Metabolic Correction of Fucosidosis Lymphoid Cells by Galaptin-α-L-Fucosidase Conjugates," Biochem. Biophys. Res. Communi., 172(1):335-340 (1990).

Amalfitano et al., "Recombinant Human Acid Alpha-Glucosidase Enzyme Therapy for Infantile Glycogen Storage Disease Type II: Results of a Phase I/II Clinical Trial," Genet. Med. 3(2):132-138 (2001).

Anand, "The Cure", HarperCollins, New York, NY, Chapter 23, pp. 257-268 (2006).

Arai et al., "Conformations of Variably Linked Chimeric Proteins Evaluated by Synchrotron X-ray Small-Angle Scattering," Proteins: Structure, Function, and Bioinformatics, 57:829-838 (2004).

Armstrong et al., "Uptake of Circulating Insulin-Like Growth Factor-I Into the Cerebrospinal Fluid of Normal and Diabetic Rats and Normalization of 1GF-II mRNA Content in Diabetic Rat Brain," Journal of Neuroscience Research, 59:649-660 (2000).

Auletta et at, "Receptor-mediated endocytosis and degradation of insulin-like growth factor I and II in neonatal rat astrocytes", Journal of Neuroscience Research, 31:14-20 (1992).

Authier et al., "In vitro endosome-lysosome transfer of dephosphorylated EGF receptor and Shc in rat liver," FEBS Letters, 00:25-31 (1999).

Bach et al., "Binding of Mutants of Human Insulin-like Growth Factor II to Insulin-like Growth Factor Binding Proteins 1-6," J. Biol. Chem., 268(12):9246-9254 (1993).

Bartlett et al., "CAVEAT: A Program to Facilitate the Structure-derived Design of Biologically Active Molecules," in Molecular Recognition: Chemical and Biological Problems, 182-196 (1989).

Barton et al., "Therapeutic response to intravenous infusions of glucocerebrosidase in a patient with Gaucher disease," Proc Natl Acad Sci USA, 85(5):1913-1916 (Mar. 1990).

Baxter, "Insulin-like Growth Factor (IGF)-Binding Proteins: Interactions with IGFs and Intrinsic Bioactivities." Am. J. Physiol. Endocrinol. Metab., 278(6)967-976 (2000).

Becker et al., "HLA and Mate Choice," J. Hum. Genet., 62:991 (1998).

Beljaars et al., "Characteristics of the hepatic stellate cell-selective carrier mannose 6-phosphate modified albumin (M6P28-HSA)," Liver, 21:320-328 (2001).

Beutler et al., "Gaucher Disease," in The Metabolic and Molecular Bases of Inherited Disease, 8th ed., 3635-3668 (2001).

Bickel et al., "Delivery of Peptides and Proteins through the Blood-Brain Barrier," Advanced Drug Delivery Reviews 46(1-3):247-279 (2001).

Bijsterbosch et al., "Native and Modified Lipoproteins as Drug Delivery Systems," Advanced Drug Delivery Reviews, 5:231-251 (1990).

Bijvoet et al., "Expression of cDNA-Encoded Human Acid Alpha-Glucosidase in Milk of Transgenic Mice," Biochim. Biophys. Acta, 1308(2):93-96 (1996).

Bijvoet et al., "Human Acid Alpha-Glucosidase from Rabbit Milk Has Therapeutic Effect in Mice with Glycogen Storage Disease Type II," Hum. Mol. Genet., 8(12):2145-2153 (1999).

Bijvoet et al., "Recombinant Human Acid Alpha-Glucosidase: High Level Production in Mouse Milk, Biochemical Characteristics, Correction of Enzyme Deficiency in GSDII KO Mice," Hum. Mol. Genet., 7(11):1815-1824 (1998).

Birkenmeier et al., "Increased Life Span and Correction of Metabolic Defects in Murine Mucopolysaccharidosis Type VII after Syngeneic Bone Marrow Transplantation," Blood, 78(11):3081-3092 (1991).

Birkenmeier et al., "Murine Mucopolysaccharidosis Type VII; Characterization of a Mouse with β-Glucuronidase Deficiency," J. Clin. Invest., 83(4):1258-1266 (1989).

Bishop et al., "Human a-Galactosidase Characterization and Eukaryotic Expression of the Full-length cDNA and Structural Organization of the Gene," in Lipid Storage Disorders Biological and Medical Aspects, vol. 150:809-822 (1987).

Blakey et al., "Effect of Chemical Deglycosylation of Ricin A Chain on the in Vivo Fate and Cytotoxic Activity of an Immunotoxin Composed of Ricin A Chain and Anti-Thy 1.1 Antibody," Cancer Research, 47:947-952 (1987).

Brady et al., "Enzyme replacement therapy in Fabry disease," J. Inherit, Metab. Dis., 24:18-24 (2001).

Braulke, "Type-2 IGF Receptor: A Multi-Ligand Binding Protein," Horm. Metab. Res., 31:242-246 (1999).

Brooks et al., "Functional correction of established central nervous system deficits in an animal model of lysosomal storage disease with feline immunodeficiency virus-based vectors," PNAS Early Editiion, 1-6 (2002).

Brooks, "Immune Response to Enzyme Replacement Therapy in Lysosomal Storage Disorder Patients and Animal Models," Mol. Genet. Metab., 68:268-275 (1999).

Brown et al., "Structure of a Functional IGF2R Fragment Determined from the Anomalous Scattering of Sulfur," EMBO J., 21(5):1054-1062 (2002).

Bungard, Design of Prodrugs, pp. 7-9, 21-24, Elsevier, Amsterdam (1985).

Burgisser et al., "Mutants of Human Insulin-like Growth Factor II with Altered Affinities for the Type 1 and Type 2 Insulin-like Growth Factor Receptor," J. Biol. Chem., 266(2):1029-1033 (1991).

Cacciari et al., "Somatomedin C in Pediatric Pathophysiology," Pediatrician, 14:146-153 (1987).

Calhoun et al., "Fabry Disease: Isolation of a cDNA Clone Encoding Human α-Galactosidase A," Proc. Natl. Acad. Sci. USA, 82:7364-7368 (1985).

Cascieri et al., "Structural Analogs of Human Insulin-like Growth Factor (IGF) I with Altered Affinity for Type 2 IGF Receptors," J. Biol. Chem., 264(4):2199-2202 (1999).

Chodobski et al., "Choroid Plexus: Target for Polypeptides and Site of Their Synthesis,"Microscopy Research and Technique, 52:65-82 (2001).

Connolly-Martin, "Computer-Assisted Rational Drug Design," Methods in Enzymology 203:587-613 (1991).

Dahms et al., "Mannose 6-Phosphate Receptors and Lysosomal Enzyme Targeting," The Journal of Biological Chemistry, 264(21):12115-12118 (1989).

Daly et al., "Neonatal Gene Transfer Leads to Widespread Correction of Pathology in a Murine Model of Lysosomal Storage Disease," Proc. Natl. Acad. Sci. USA 96(5):2296-2300 (1999).

Desnick et al., "Enzyme Replacement and Enhancement Therapies: Lessons from Lysosomal Disorders", Nature Reviews Genetics, 3:954-966 (Dec. 2002).

Devedjian et al., "Transgenic mice overexpressing insulin-like growth factor-II in f3 cells develop type 2 diabetes," The Journal of Clinical Investigation 105(6):731-740 (2000).

Devi et al., "An Insulin-Like Growth Factor II (IGF-II) Affinity-Enhancing Domain Localized within Extracytoplasmic Repeat 13 of the IGF-II/Mannose 6-Phosphate Receptor," Molecular Endocrinology, 12(11):1661-1672 (1998).

Difalco et al., "Efficacy of an Insulin-Like Growth Factor-Interleukin-3 Fusion Protein in Reversing the Hematopoietic Toxicity Associated with Azidothymidine in Mice," The Journal of Pharmacology and Experimental Therapeutics, 284:449-454 (1998).

Difalco et al., "Preparation of a recombinan chimaera of insulin-like growth factor II and interleukin 3 with highproliferative potency for haemopoietic cells," Biochem. J., 326:407-413 (1997).

Diment et al., "Generation of Macrophage Variants with 5-Azacytidine: Selection for Mannose Receptor Expression," J. Leukocyte Biol. 42:485-490 (1987).

Dixon, "Computer-Aided Drug Design: Getting the Best Results," TIBTECH, 10:357-363 (1992).

Dobrenis et al., "Neuronal Lysosomal Enzyme Replacement Using Fragment C of Tetanus Toxin," Proc. Natl. Acad. Sci. USA, 89:2297-2301 (1992).

Douglass et al., "Chemical Deglycosylation Can Induce Methylation, Succinimide Formation, and Isomerization" J. Protein Chem., 20(7):571-576 (2001).

Duguay et al., "Post-translational Processing of the Insulin-like Growth Factor-2 Precursor," J. Biol. Chem., 273(29):18443-18451 (1998).

Dziegielewska et al., "The ins and outs of brain-barrier mechanisms," Trends in Neurosciences, 25(2):69-71 (2002).

Eisen et al., "HOOK: A Program for Finding Novel Molecular Architectures That Satisfy the Chemical and Steric Requirements of a Macromolecule Binding Site" Proteins: Structure, Function, and Genetics, 19:199-221 (1994).

European Search Report for EP02801739 (2005).

European Search Report for EP08000935 (2008).

European Supplementary Partial Search Report for European Application No. EP 03 73 6779 (Date of mailing Apr. 5, 2007).

Forbes et al., "Contribution of Residues A54 and L55 of the Human Insulin-like Growth Factor- II (IGF-II) a Domain to Type 2 IGF Receptor Binding Specificity," Growth Factors, 19:163-173 (2001).

Foxwell, et al., "The Preparation of Deglycosylated Ricin by Recombination of Glycosidase Treated A- and B-Chains: Effects of Deglycosylation on Toxicity and in vivo Distribution," Biochemica et Biophysica Acta, 923:59-65 (1987).

Friden et al., "Anti-Transferrin Receptor Antibody and Antibody-Drug Conjugates Cross the Blood-Brain Barrier," Proc. Natl. Acad. Sci. USA, 88:4771-4775 (1991).

Fukuda et al., "Dysfunction of Endocytic and Autophagic Pathways in a Lysosomal Storage Disease," Ann. Neurol., 59(4):700-708 (2006).

Fukuda et al., "Autophagy and Lysosomes in Pompe Disease," Autophagy, 2(4):318-320 (2006).

Fukuda et al., "Autophagy and Mistargeting of Therapeutic Enzyme in Skeletal Muscle in Pompe Disease," Mol. Therapy, 14(6):831-839 (2006).

Fukuta et al., "Insulin Fragments as a Carrier for Peptide Delivery Across the Blood-Brain Barrier," Pharmaceutical Research, 11(12):1681-1688 (1994).

Godar et al., "M6P/IGFII-Receptor Complexes Urokinase Receptor and Plasminogen for Activation of Transforming Growth Factor-β1," Eur. J. Immunol., 29:1004-1013 (1999).

Golden et al., "Human Blood-Brain Barrier Leptin Receptor," J. Clin. Invest., 99(1):14-18 (1997).

Gozes et al., "Neuropeptides: brain messengers of many faces," Trends in Neurosciences, 24(12):687-690 (2001).

Grimme et al., "Endocytosis of Insulin-like Growth Factor II by a Mini-receptor Based on repeat 11 of the Mannose 6-Phosphate/Insulin-like Growth Factor II Receptor," J. Biol. Chem., 275(43):33697-33703 (2000).

Grubb et al., "Large Scale Purification of Phosphorylated Recombinant β-Glucuronidase from Over-Expressing Mouse L Cells," Fed. Am. Soc. Exp. Biol. 7:1255a (1993).

Hashimoto et al., "Binding Sites and Binding Proteins of Binary and Ternary Complexes of Insuline-like Growth Factor II (IGF-II), IGF-binding Protein-3, and Acid-labile Subunit," J. Biol. Chem., 272(44):27936-42 (1997).

Hashimoto et al., "N-terminal Deletion Mutants of Insulin-like Growth Factor-II (IGF-II) Show Thr7 and Leu8 Important for Binding to Insulin and IGF-I Receptors and Leu8 Critical for All IGF-II Functions," J. Biol. Chem., 270(30):18013-18018 (1995).

Haskell et al., "Intracellular Trafficking of the JNCL Protein CLN3," Molecular Genetics and Metabolism, 66:253-260 (1999).

Henikoff and Henikoff, "Amino acid substitution matrices from protein blocks," PNAS, 89:10915-10919 (1992).

Hickman et al., "A Recognition Marker Required for Uptake of a Lysosomal Enzyme by Cultured Fibroblasts," BBRC, 57:55-61 (1974).

Hirschhorn et al., "Glycogen Storage Disease Type II: Acid a-Glucosidase (Acid Maltase) Deficiency," in the Metabolic and Molecular Basis of Inherited Disease, 8th ed., 3389-3420 (2001).

Hoefsloot et al., "Expression and Routeing of Human Lysosomal Alpha-Glucosidase in Transiently Transfected Mammalian Cells," Biochem. J., 272 (2):485-492 (1990).

Houba et al., "Improved Characteristics of a Human β-Glucuronidase—Antibody Conjugate after Deglycosylation for Use in Antibody-Directed Enzyme Prodrug Therapy," Bioconiugate Chem. 7:606-611 (1996).

International Search Report for PCT/US02/13835 (2002).
International Search Report for PCT/US02/32968 (2002).
International Search Report for PCT/US02/32996 (2002).
International Search Report for PCT/US03/17211 (2003).
International Search Report for PCT/US2007/023881 (2009).

Ishibashi et al., "Asialoglycoprotein Receptor Deficiency in Mice Lacking the Minor Receptor Subunit," J. Biol. Chem. 269(45):27803-27806(1994).

Islam et al., "C-terminal Processing of Human β-Glucuronidase," J. Biol. Chem., 268(30): 22627-22633 (Oct. 1993).

Jacob et al., "Sucrase Is an Intramolecular Chaperone Located at the C-terminal End of the Sucrase-Isomaltase Enzyme Complex," J. Biol. Chem., 277:32141 (2002).

Journet et al., Proteomic analysis of human lysosomes: Application to monocytic and breast cancer cells, Proteomics 2, 1026-1040 (2002).

Juuti-Uusitalo et al., "Selective Targeting of Avidin/Mannose 6-Phosphate Receptor Chimeras to Early or Late Endosomes," European Journal of Cell Biology, 79:458-468 (2000).

Kang et al., "Mannose 6-Phosphate/Insulin-like Growth Factor II Receptor Mediates the Growth-Inhibitory Effects of Retinoids," Cell Growth & Differentiation, 10:591-600 (1999).

Kang et al., "Mannose-6-phosphate/Insulin-like Growth Factor-II Receptor is a Receptor for Retinoic Acid," Proc. Natl. Acad. Sci. USA, 95:13671-13676 (1998).

Kang et al., "Retinoic Acid Alters the Intracellular Trafficking of the Mannose-6 Phosphate/Insulin-like Growth Factor II Receptor and Lysosomal Enzymes," Proc. Natl. Acad. Sci. USA 95:13687-13691 (1998).

Kerr et al., "Comparison of recombinant and synthetically formed monoclonal antibody beta lactamase conjugates for anticancer prodrug activation," Bioconjugate Chemistry, 10:1084-1089 (1999).

Kiess et al., "Biochemical Evidence that the Type II Insulin-like Growth Factor Receptor Is Identical to the Cation-independent Mannose 6-Phosphate Receptor," J. Biol. Chem., 263:9339-9344 (1988).

Kiess et al., "Insulin-Like Growth Factor II (IGF-II) and the IGF-II/Mannose-6-Phosphate Receptor: the Myth Continues," Horm. Res., 41(suppl. 2):66-73 (1994).

Kikuchi et al., "Clinical and Metabolic Correction of Pompe Disease by Enzyme Therapy in Acid Maltase-Deficient Quail," J. Clin. Invest. 101(4):827-833 (1998).

Kim et al., "High-Level Expression and Simple Purification of Recombinant Human Insulin-Like Growth Factor I," Journal of Biotechnology, 48:97-105 (1996).

Kishani et al., "Recombinant human acid α-glucosidase, Major Clinical Benefits in Infantile-Onset Pompe Disease," Neurology, 68:99-109 (2007).

Kishnani et al., "A Retrospective, Multilational, Multicenter Study on the Natural History of Infantile-Onset Pompe Disease," J Pediatr, 148:671-6 (2006).

Kishnani et al., "Chinese Hamster Ovary Cell-Derived Recombinant Human Acid α-Glucosidase in Infantile-Onset Pompe Disease," J Pediatr, 148:671-6 (2006).

Korner et al., "Mannose 6-Phosphate/Insulin-like Growth Factor II Receptor Fails to Interact with G-proteins," The Journal of Biological Chemistry, 270(1):287-295 (1995).

Kundra et al., "Asparagine-linked Oligosaccharides Protect Lamp-1 and Lamp-2 from Intracellular Proteolysis," J. Biol. Chem., 274(43):31039-31046 (1999).

Langford et al., "Leishmania: Codon Utilization of Nuclear Genes," Experimental Parasitology, 74:360-361 (1992).

Lau et al., "Loss of the Imprinted IGF2/Cation-Independent Mannose 6—Phosphate Receptor Results in Fetal Overgrowth and Perinatal Lethality," Genes & Development 8(24):2953-2963 (1994).

Lebowitz et al., "Glycosylation-independent targeting enhances enzyme delivery to lysosomes and decreases storage in mucopolysaccharidosis type VII mice," PNAS USA, 101:3083-3088 (2004).

Lebowitz, "A breach in the blood-brain barrier," PNAS, 102(41):14485-14486 (2005).

Lee et al., "Mannose Receptor—Mediated Regulation of Serum Glycoprotein Homeostasis," Science, 295:1898-1901 (2002).

Lemansky et al., "Synthesis and Processing of a-Galactosidase A in Human Fibroblasts," J. Biol. Chem., 262:2062-2065 (1987).

Linnell et al., "Real Time Kinetics of Insulin-like Growth Factor II (IGF-II) Interaction with the IGF-II/Mannose 6-Phosphate Receptor," The Journal of Biological Chemistry, 276(26):23986-23991, (2001).

Liu et al., "Intranasal administration of insulin-like growth factor-I bypasses the blood-brain barrier and protects against focal cerebral ischemic damage," Journal of the Neurological Sciences, 187: 91-97 (2001).

Ludwig et al., "Mouse Mutants Lacking the Type 2 IGF Receptor (IGF2R) Are Rescued from Perinatal Lethality in Igf2 and Igf1r Null Backgrounds," Developmental Biology, 177(2):517-535 (1996).

Ludwig et al., "Roles for Mannose-6-Phosphate Receptors in Lysosomal Enzyme Sorting, IGF-II Binding and Clathrin-Coat Assembly," Trends in Cell Biology, 5:202-206 (1995).

Luthi et al., "Mutants of Human Insulin-like Growth Factor II (IGF II) Expression and Characterization of Truncated IGF II and of Two Naturally Occurring Variants," Eur. J. Biochem. 205(2):483-490 (1992).

Lynch et al., "High-resolution Light Microscopy (HRLM) and Digital Analysis of Pompe Disease Pathology," J. Histochem. Cytochem., 53:63-73 (2005).

Magee et al., "Insulin-like Growth Factor I and Its Binding Proteins: A Study of the Binding Interface Using B-Domain Analogues," Biochemistry, 38(48):15863-15870 (1999).

Mah et al., "Physiological Correction of Pompe Disease by Systemic Delivery of Adeno-associated Virus Serotype 1 Vectors," Molecular Thereapy (online publication) (2007).

Mahuran et al., "Proteolytic Processing of Pro-a and Pro-B Precursors from Human B-Hexosaminidase," J. Biol. Chem., 263:4612-4618 (1988).

Martiniuk et al., "Correction of Glycogen Storage Disease Type II by Enzyme Replacement with a Recombinant Human Acid Maltase Produced by Over-Expression in a CHO-DHFR(neg) Cell Line," Biochem. Biophys. Res. Commun., 276(3):917-923 (2000).

Martiniuk et al., "Recombinant Human Acid α-Glucosidase Generated in Bacteria: Antigenic, but Enzymatically Inactive," DNA and Cell Biology, 11(9):701-706 (1992).

Mazzolla et al., "Enhanced Resistance to Cryptococcus neoformans Infection Induced by Chloroquine in a Murine Model of Meningoencephalitis," Antimicrobial Agents and Chemotherapy, 41:802-807 (1997).

Meynial-Salles et al., "In vitro glycosylation of proteins: an enzymatic approach," J. Biotechnology, 1-14 (1996).

Moreland et al., "Lysosomal Acid α-Glucosidase Consists of Four Different Peptides Processed from a Single Chain Precursor," J. Biol. Chem, 280:6780-6791 (2005).

Morgan et al., "Insulin-like Growth Factor II Receptor as a Multifunctional Binding Protein," Nature 329(6137):301-307 (1987).

Myszka, "Kinetic, Equilibrium, and Thermodynamic Analysis of Macromolecular Interactins with BIACORE," Methods Enzymol., 323:325-340 (2000).

Newrzella et al., "Functional analysis of the glycosylaton of murine acid sphingomyenlinase," J. Biol. Chem., 271:32089-32095 (1996).

Nilsson et al., N. Engl. J. Med., 318:947-50 (1988).

Nissley at al., "Reciprocal modulation of binding of lysosomal enzymes and insulin-like growth factor-II (IGF-II) to the mannose 6-phosphate/IGF-II receptor," Adv. Exp. Med. Biol., 293:311-324 (1991).

Niwa et al., "Efficient Selection for High-Expression Transfectants with a Novel Eukaryotic Vector," Gene 108:193-200 (1991).

Nolan et al., "Binding of Insulin-Like Growth Factor II (IGF-II) by Human Cation-Independent Mannose 6-Phosphate Receptor/IGS-II Receptor Express in Receptor-Deficient Mouse L Cells," Cell Regulation, 1(2):197-213 (Jan. 1990).

Novazyme Website printouts (2001).

Nykjaer et al., "Mannose 6-Phosphate/Insulin-like Growth Factor-II Receptor Targets the Urokinase Receptor to Lysosomes via a Novel Binding Interaction," The Journal of Cell Biology 141(3):815-828 (1998).

O'Connor et al., "Enzyme Replacement Therapy for Murine ucopolysaccharidosis Type VII Leads to Improvements in Behavior and Auditory Function," J. Clin. Invest., 101:1394-1400 (1998).

O'Dell et al., "Molecules in Focus Insulin-like Growth Factor II (IGF-II)," The International of Biochemistry & Cell Biology, 30(7):767-771 (1998).Journal.

Oksche et al., "Late Endosomal/Lysosomal Targeting and Lack of Recycling of the Ligand-Occupied Endothelin B Receptor," Molecular Pharmacology 57:1104-1113 (2000).

Paasche et al., "Mechanisms of Endothelin Receptor Subtype-specific Targeting to Distinct Intracellular Trafficking Pathways," The Journal of Biological Chemistry, 276(36):34041-34050 (2001).

Pardridge, "Drug Delivery to the Brain," Journal of Cerebral Blood Flow and Metabolism, 17:713-731 (1997).

Pardridge, "Targeting Neurotherapeutic Agents Through the Blood-Brain Barrier," Arch Neural., 59: 35-40 (2002).

Pauly et al., "Complete correction of acid $\alpha$-glucosidase deficiency in Pompe disease fibroblasts in vitro, and lysosomally targeted expression in neonatalrat cardiac and skeletal muscle," Gene Therapy, 5:473-480 (1998).

PCT International Preliminary Report on Patentability for International Application No. PCT/US05/004286 (Date of issuance Aug. 14, 2006).

PCT International Search Report for International Application No. PCT/US05/004286 (Date of mailing Aug. 31, 2005).

Pine, Organic Chemistry, 5th ed., McGraw Hill, p. 770 (1987).

Poznansky et al., "Enzyme Replacement Therapy in Fibroblasts from a Patient with Cholesteryl Ester Storage Disease," FASEB J., 3:152-156 (1989).

Prince et al., "Lipoprotein Receptor Binding, Cellular Uptake, and Lysosomal Delivery of Fusions between the Receptor-associated Protein (RAP) and $\alpha$-L-Iduronidase or Acid $\alpha$-Glucosidase," J. Biol. Chem., 279(33):35037-35046 (2004).

Pulford et al., "Uptake of Circulating Insulin-Like Growth Factors (IGFs) into Cerebrospinal Fluid Appears to Be Independent of the IGF Receptors as Well as IGF-Binding Proteins " Endocrinology, 142(1):213-220 (2001).

Raben et al., "Acid $\alpha$-Glucosidase Deficiency (Glycogenosis Type II, Pompe Disease)," Current Molecular Medicine, 2:145-166 (2002).

Raben, JBC, 273:19086-19092 (1998).

Ramalingam et al., "Binding to the transferrin receptor is required for endocytosis of HFE and regulation of iron homeostasis," Nature Cell Biology, 2(12):953-957 (2000).

Reinherdt and Bondy, "Insulin-Like Growth Factors Cross the Blood-Brain Barrier," Endocrinology, 135:1753-1761 (1994).

Reuser et al., "Biochemical, Immunological, and Cell Genetic Studies in Glycogenosis Type II," Am. J. Hum. Genet. 30(2):132-143 (1978).

Rocca et al., "Involvement of the Ubiquitin/Proteasome System in Sorting of the Interleukin 2 Receptor $\beta$ Chain to Late Endocytic Compartments," Molecular Biology of the Cell, 12:12931301 (2001).

Rohyt, Essentials of carbohydrate chemistry, Springer-Verlag: New York, p. 34-35 (1998).

Rohyt, Essentials of carbohydrate chemistry, Springer-Verlag: New York, p. 350 (1998).

Rosenberg, et al., "Immunosurveillance of Alglucerase Enzyme Therapy for Gaucher Patients: Induction of Humoral Tolerance in Seroconverted Patients after Repeat Administration," Blood, 93(6):2081-2088 (1999).

Roth et al., "Mutants of Human Insulin-like Growth Facto II: Expression and Characterization of Analogs with a Substitution of TYR27 and/or a Deletion of Residues 62-67," Biochem. Biophys. Res. Commun., 181(2):907-914 (1991).

Russell et al., "Recombinant proteins for genetic disease," Clinical Genetics, 55:389-394 (1999).

Sakano et al., "The Design, Expression, and Characterization of Human Insulin-like Growth Factor II (IGF-II) Mutants Specific for Either the IGF-II/Cation-independent Mannose 6-Phosphate Receptor or IGF-I Receptor" The Journal of Biological Chemistry, 266(31):20626-20635 (1991).

Samoylova et al., "Elucidation of Muscle-Binding Peptides by Phage Display Screening," Muscle and Nerve, 22:460 (1999).

Sandoval et al., "Enhanced proliferative effects of a baculovirus-produced fusion protein of insulin-like growth factor and $\alpha_1$—proteinase inhibitor and improved anti-elastase activity of the inhibitor with glutamate at position 351," Protein Engineering, 15(5):413-418 (2002).

Sandoval et al., "The fusion of IGF I with stromal cell-derived factor I or $\alpha$1 proteinase inhibitor alters their mitogenic or chemotactic activities while keeping their ability to inhibit HIV-1-gp120 binding," Biochemical Pharmacology, 65:2055-2063 (2003).

Sands et al., "Biodistribution, Kinetics, and Efficacy of Highly Phosphorylated and Non-phosphorylated $\beta$-Glucuronidase in the Murine Model of Mucopolysaccharidosis VII," J. Biol. Chem., 276(46):43160-43165 (2001).

Sands et al., "Enzyme Replacement Therapy for Murine Mucopolysaccharidosis Type VII," J. Clin. Invest., 93(6):2324-2331 (1994).

Sands et al., "Murine Mucopolysaccharidosis Type VII: Long Term Therapeutic Effects of Enzyme Replacement and Enzyme Replacement Followed by Bone Marrow Transplantation," J. Clin. Invest., 99:1596-1605 (1997).

Shin et al., "Functional Properties of Antibody Insulin-like Growth Factor Fusion Proteins " J. Biol. Chem., 269(7):4979-4985 (1994).

Shipley et al., "The Role of Glycosylation and Phosphorylation in the Expression of Active Human $\beta$-Glucuronidase," J. Biol. Chem. 268(16):12193-12198 (1993).

Silverman, The Organic Chemistry of Drug Design and Drug Action, pp. 352-401, Academic Press, San. Diego, Calif. (1992).

Sly et al., "Active Site Mutant Transgene Confers Tolerance to Human $\beta$-Glucuronidase without Affecting the Phenotype of MPS VII Mice," PNAS, 98(5):2205-2210 (2001).

Smith and Waterman, "Identification of Common Molecular Subsequences," Journal of Molecular Biology, 147:195-197 (1981).

Smith et al., "Structure and Activity Dependence of Recombinant Human Insulin-like Growth Factor II on Disulfide Bond Pairing," The Journal of Biological Chemistry, 264(16):9314-9321 (1989).

Sohar et al., "Mouse Mutants Lacking the Cation-Independent Mannose 6-Phosphate/Insulin-Like Growth Factor II Receptor are Impaired in Lysosomal Enzyme Transport: Comparison of Cation-Independent and Cation-Dependent Mannose 6-Phosphate Receptor-Deficient Mice," Biochem. J., 330:903-908 (1998).

Sojar et al., "Characterization of Rat Ovarian Lutropin Receptor," J. Biol. Chem., 264(5):2552-2559 (1989).

Sojar et al., "Chemical Deglycosylation of Glycoproteins," Methods in Enzymology 138:341-350 (1987).

Soper et al., "Enzyme Replacement Therapy Improves Reproductive Performance in Mucopolysaccharidosis Type VII Mice, but Does Not Prevent Postnatal Losses," Pediatr. Res.45(2):180-186 (1999).

Souriau et al., "Direct Selection of EGF Mutants Displayed on Filamentous Phage Using Cells Overexpressing EGF Receptor," Biol. Chem., 380(4): pp. 451-458 (1999).

Sperr et al., "Rituximab for the treatment of acquired antibodies to factor VIII," Haematologica, 92(1):66-71 (Jan. 2007).

Spiro et al., "Characterization of Carbohydrate Units of Glycoproteins," Methods Enzymol. 8: 44-49 (1966).

Spodsberg, "Molecular Basis of Aberrant Apical Protein Transport in an Instestinal Enzyme Disorder," J. Biol. Chem., 276:23506 (2001).

Stahl et al., "Evidence for Specific Recognition Sites Mediating Clearance of Lysosomal Enzymes in vivo," PNAS 73(11):4045-4049 (1976).

Standley et al., "The role of glycosylation in ionotropic glutamate receptor ligand binding, function, and trafficking," Cellular and Molecular Life Sciences, 57:1508-1516 (1998).

Stanley et al., "Chinese Hamster Ovary Cells Selected for Resistance to the Cytotoxicity of Phytohemagglutinin are Deficient in a UDP-N-Acetylglucosamine-Glycoprotein N-Acetylglucosaminyltransferase Activity," Proc. Natl. Acad. Sci. USA 72(9):3323-3327 (1975).

Stanley et al., "Selection and Characterization of Eight Phenotypically Distinct Lines of Lectin-Resistant Chinese Hamster Ovary Cell" Cell, 6(2):121-128 (1975).

Summary of the Boston IPA Board Meeting Apr. 16-17, 2002, Association for Glycogen Storage Disease (UK) Bulletin, Issue 9, May 2002, p. 14.

Supplementary European Search Report for EP 02 72 5886 (2004).

Terasawa et al., "Solution Structure of Human Insulin-like Growth Factor II; Recognition Sites for Receptors and Binding Proteins," The EMBO Journal 13(23):5590-5597 (1994).

The Cytokine Facts Book (Second Ed. Academic Press, 2001). pp. 301-305; the page cited is included in form 892 and as 'appendix A'.

Thim, "A new family of growth factor-like peptides Trefoil disulphide loop structures as a common feature in breast cancer associated peptide (pS2), pancreatic spasmolytic polypeptide (PSP), and frog skin peptides (spasmolysins)," FEBS Lett., 250:85 (1989).

Thorpe et al., "Modification of the Carbohydrate in Ricin with Metaperiodate—Cyanoborohydride Mixtures," Eur. J. Biochem. 147:197-206 (1985).

Thotakura et al., "Enzymatic Deglycosylation of Glycoproteins," Methods in Enzymology, 138:350-359 (1987).

Thurgerg et al., "Characterization of pre- and post-treatment pathology after enzyme replacement therapy for pompe disease," Lab. Invest., 86:1208-1220 (2006).

Timmermans et al., "Angiotensin II Receptors and Angiotensin II Receptor Antagonists," Pharmacological Reviews 45(2):205-251 (1993).

Tong et al., "The Cation-independent Mannose 6-Phosphate Receptor Binds Insulin-like Growth Factor II," The Journal of Biological Chemistry, 263(6):2585-2588 (1988).

Torres et al., "Solution Structure of Human Insulin-like Growth Factor II. Relationship to Receptor and Binding Protein Interactions," J. Mol. Biol. 248(2):385-401 (1995).

Tschinke et al., "The NEWLEAD Program: A New Method for the Design of Candidate Structures from Pharmacophoric Hypotheses," J. Med. Chem., 36:3863-3870 (1993).

Tsuji et al., "Intracellular Transport of Acid $a$-Glucosidase in Human Fibroblasts: Evidence for Involvement of Phosphomannosyl Receptor-Independent System," J. Biochem., 104(2):276-278 (1988).

Tsuji et al., "Lysosomal Enzyme Replacement Using $a_2$-Macroglobulin as a Transport Vehicle," J. Biochem., 115:937-944 (1994).

Tsuji et al., "The Precursor of Acid $a$-Glucosidase is Synthesized as a Membrane-Bound Enzyme," Biochem. Int., 15(5):945-952 (1987).

Ulmasov et al., "Purification and Kinetic Analysis of Recombinant CA XII, a Membrane Carbonic Anhydrase Overexpressed in Certain Cancers," PNAS, 97(26):14212-14217 (2000).

Urayama et al., "Developmentally regulated mannose 6-phosephate receptor-mediated transport of a lysosomal enzyme across the blood-brain barrier," PNAS (USA), 101:12658-12663 (2004).

Vaccaro, Karen, email dated Feb. 20, 2002.

Valenzano et al., "Biophysical and Biological Properties of Naturally Occurring High Molecular Weight Insulin-like Growth Factor II Variants," J. Biol. Chem., 272(8):4804-4813 (1997).

Valenzano et al., "Soluble Insulin-like Growth Factor II/Mannose 6-Phosphate Receptor Carries Multiple High Molecular Weight Forms of Insulin-like GrowthFactor II in Fetal Bovine Serum," J. Biol. Chem.,270(27):16441-16448 (1995).

Van Den Hout et al., "Enzyme Therapy for Pompe Disease with Recombinant Human $a$-Glucosidase from Rabbit Milk," J: Inherit. Metab. Dis., 24(2):266-274 (2001).

Van Den Hout et al., "Recombinant Human $a$-Glucosidase from Rabbit Milk in Pompe Patients," Lancet 356(9227):397-398 (2000).

Van Der Ploeg et al., "Intravenous Administration of Phosphorylated Acid a-Glucosidase Leads to Uptake of Enzyme in Heart and Skeletal Muscle of Mice," J. Clin. Invest., 87:513-518 (1991).

Van Doorn et al., "Antibodies Directed against the E Region of Pro-Insulin-like Growth Factor-11 Used to Evaluate Non-Islet Cell Tumor-induced Hypoglycemia,"Clinical Chemistry, 48(10):1739-1750 (2002).

Van Hove et al., "High-Level Production of Recombinant Human Lysosomal Acid $a$-Glucosidase in Chinese Hamster Ovary Cells which Targets to Heart Muscle and Corrects Glycogen Accumulation in Fibroblasts from Patients with Pompe Disease," Proc. Natl. Acad. Sci. USA, 93(1):65-70 (1996).

Vogler et al., "A Murine Model of Mucopolysaccharidosis VII," Am. J. Pathol., 136(1):207-217 (1990).

Vogler et al., "Enzyme Replacement with Recombinant B-glucuronidase in the Newborn Mucopolysaccharidosis Type VII Mouse," Pediatric Research, 34(6):837-840 (1993).

Vogler et al., "Overcoming the blood-brain barier with high-dose enzyme replacement therapy in murine mucopolysaccharidosis VII," PNAS USA 10.1073/pnas.0506892102, 6 pages, (2005).

Vyas et al., "Ligand-Receptor-Mediated Drug Delivery: An Emerging Paradigm in Cellular Drug Targeting," Critical ReviewsTM in Therapeutic Drug Carrier Systems 18(1):1-76 (2001).

Wadensten et al., "Purification and Characterization of Recombinant Human Insulin-like Growth Factor II (IGF-II) Expressed as a Secreted Fusion Protein in *Escherichia coli*," Biotechnology and Applied Biochemistry, 13(3):412-421 (1991).

Waheed et al., "Human Lysosomal Acid Phosphatase is Transported as a Transmembrane Protein to Lysosomes in Transfected Baby Hamster Kidney Cells," EMBO J., 7(8):2351-2358 (1988).

Waheed et al., "Regulation of Transferrin-Mediated Iron Uptake by HFR, the Protein Defective in Hereditary Hemochromatosis," PNAS 99(5):3117-3122 (2002).

Wang et al., "A study of protein-protein interactions in living cells using luminescence resonance energy transfer (LRET) from Renilla luciferase to Aequorea GFP," Mol. Gen. Genet., 264:578-587 (2001).

Wang et al., "Regulation of Embryonic Growth and Lysosomal Targeting by the Imprinted *Igf2/Mpr* Gene," Nature, 372(6505):464-467 (1994).

Wang et al., "The Insulin A and B Chains Contain Sufficient Structural Information to Form the Native Molecule," Trends in Biochemical Sciences 16:279-281 (1991).

Waszkowycz et al., "PRO_LIGAND: An Approach to de Novo Molecular Design. 2. Design of Novel Molecules from Molecular Field Analysis (MFA) Models and Pharmacophores," J. Med. Chem., 37:3994-4002 (1994).

Wilczak et al., "Insulin-like growth factor system in serum and cerebrospinal fluid in patients with multiple sclerosis," Neuroscience letters, 257:168-170 (1998).

Williams et al.,Enzymes Replacement in Pompe Disease With an α-Glucosidase-Low Density Lipoprotein Complef; XVI(1):415-423 (1980).

Willingham et al., "The Receptosome: an Intermediate Organelle of Receptor-Mediated Endocytosis in Cultured Fibroblasts," Cell, 21(1):67-77 (1980).

Wisselaar et al., "Structural and Functional Changes of Lysosomal Acid $a$-Glucosidase during Intracellular Transport and Maturation," J. Biol. Chem., 268(3):2223-2231 (1993).

Wolfe of al., "Murine Mucopolysaccharidosis Type VII: A Model System for Somatic Gene Therapy of the Central Nervous System," in Protocols for Gene Transfer in Neuroscience: Towards Gene Therapy of Neurological Disorders, Lowenstein, et al., eds., John Wiley & Sons Ltd., Chap. 20, pp. 263-274 (1996).

Written Opinion for PCT/US2005/004286 (2005).

Written Opinion for PCT/US2007/023881 (2009).

Yamashiro et al., "Acidification of Endocytic Compartments and the Intracellular Pathways of Ligands and Receptors," Journal of Cellular Biochemistry, 26:231-246 (1984).

Yang et al.,"Probing the Folding Pathways of Long R3 Insulin-like Growth Factor-1 (LR3IGF-1) and IGF-1 via Capture and Identification of Disulfide Intermediates by Cyanylation Methodology and Mass Spectrometry," The Journal of Biological Chemistry 274(53):37598-37604 (1999).

York et al., "The Rate of Internalization of the Mannose 6-Phosphate/Insulin-like Growth Factor II Receptor Is Enhanced by Multivalent Ligand Binding," The Journal of Biological Chemistry, 274(2):1164-1171 (1999).

Yu et al., "Insuline-Like Growth Factors (IG-I, Free IGF-I, and IGF-II) and Insulin-Like Growth Factor Binding Proteins (IGFBP-2, IGFBP-3, IGFBP-6, and ALS) in Blood Circulation," J. Clin. Lab. Anal., 13(4):166-72 (1999).

Zarn et al., "A Mutant of Human Insulin-like Growth Factor II (IGF II) with the Processing Sites of Proinsulin," Eur. J. Biochem. 210:665-669 (1992).

Zhu et al., "Carbohydrate-remodeled acid a-glucosidase with higher affinity for the cation-independent mannose 6-phosphate receptor demonstrates improved delivery to muscles of Pompe mice," Biochemical Journal, Biochem J., 389:619-628 (2005).

Zhu et al., "Conjugation of Mannose 6-Phosphate-containing Oligosaccharides to Acid α-Glucosidase Improves the Clearance of Glycogen in Pompe Mice,"The Journal of Biological Chemistry, 279(48):50336-50341 (2004).

Zubieta et al., "Response: Measuring our natural painkiller," Trends in Neurosciences, 25(2):69-71 (2002).

Kiess et al., "Insulin-Like Growth Factor II (IGF-II) Inhibits Both the Cellular Uptake of β-Galactosidase and the Binding of β-Galactosidase to Purified IGF-II/Mannose 6-Phosphate Receptor," The Journal of Biological Chemistry, 264(8):4710-4714 (1989).

Rhee et al., "High-level expression of human insulin-like growth factor II in *Escherichia coli*," Journal of Biotechnology, 13:293-304 (1990).

* cited by examiner

Alignment of human IGF-I and IGF-II mature proteins showing location of domains.

MGKISSLPTQLFKCCFCDFLKVKMHTMSSSHLFYLALCLLTFTS
SATAGPETLCGAELVDALQFVCGDRGFYFNKPTGYGSSSRRAPQTGIVDECCFRSCDL
RRLEMYCAPLKPAKSARSVRAQRHTDMPKTQKEVHLKNASRGSAGNKNYRM (SEQ ID NO:3)

FIG. 4A

```
   1 tcactgtcac tgctaaattc agagcagatt agagcctgcg caatggaata aagtcctcaa
  61 aattgaaatg tgacattgct ctcaacatct cccatctctc tggatttcct tttgcttcat
 121 tattcctgct aaccaattca tttcagact ttgtacttca gaagcaatgg gaaaaatcag
 181 cagtcttcca accaattat ttaagtgctg ctttgtgat ttcttgaagg tgaagatgca
 241 caccatgtcc tcctcgcatc tcttctacct ggcgctgtgc ctgctcacct tcaccagctc
 301 tgccacggct ggaccggaga cgctctgcgg ggctgagctg gtggatgctc ttcagttcgt
 361 gtgtggagac aggggctttt atttcaacaa gcccacaggg tatggctcca gcagtcggag
 421 ggcgcctcag acaggcatcg tggatgagtg ctgcttccgg agctgtgatc taaggaggct
 481 ggagatgtat tgcgcaccc tcaagcctgc caagtcagct cgctctgtcc gtgcccagcg
 541 ccacaccgac atgccccaaga cccagaagga agtacatttg aagaacgcaa gtagagggag
 601 tgcaggaaac aagaactaca ggatgtagga agaccctct gaggagtgaa gagtgacatg
 661 ccaccgcagg atcctttgct ctgcacgagt taccctgttaa actttggaac acctaccaaa
 721 aaataagttt gataacattt aaaagatggg cgtttccccc aatgaaaatac acaagtaaac
 781 attccaacat tgtctttagg agtgatttgc accttgcaaa aatggtcctg gagttggtag
 841 attgctgttg atctttatc aataatgttc tatagaaaag aaaaaaaaat atatatatat
 901 atatatctta gtccctgcct ctcaagagcc acaaatgcat gggtgttgta tagatccagt
 961 tgcactaaat tcctctctga atcttggctg ctggagccat tcattcagca accttgtcta
1021 agtggtttat gaattgtttc cttattgtca cttcttttcta cacaactcgg gctgtttgtt
1081 ttacagtgtc tgataatctt gttagtctat accaccacc tccctcata acctttatat
1141 ttgccgaatt tggcctcctc aaaagcagca gcaagtcgtc aagaagcaca ccaattctaa
1201 cccacaagat tccatctgtg gcatttgtac caaatataag ttggatgcat tttatttag
1261 acacaaagct ttattttttc acatcatgct tacaaaaaaag aataatgcaa atagttgcaa
1321 ctttgaggcc aatcattttt aggcatatgt tttaaacata gaaagtttct tcaactcaaa
1381 agagttcctt caaatgatga gttaatgtgc aacctaatta gtaactttcc tcttttatt
1441 ttttccatat agagcactat gtaaatttag catatcaatt atacaggata tatcaaacag
1501 tatgtaaaac tctgttttt agtataatgg tgctattttg tagtttgtta tatgaaagag
1561 tctggccaaa acggtaatac gtgaaagcaa aacaataggg gaagcctgga gccaaagatg
```

FIG. 4B-1

```
1621  acacaagggg aagggtactg aaaacaccat ccatttggga agaaaggcaa agtcccccca
1681  gttatgcctt ccaagaggaa cttcagacac aaaagtccac tgatgcaaat tggactggcg
1741  agtccagaga ggaaactgtg gaatggaaaa agcagaaggc taggaattt agcagtcctg
1801  gtttctttt ctcatggaag aaatgaacat ctgccagctg tgtcatggac tcaccactgt
1861  gtgaccttgg gcaagtcact tcacctctct gtgcctcagt ttcctcatct gcaaaatggg
1921  ggcaatatgt catctaccta cctcaaaggg gtggtataag gttaaaaag ataaagattc
1981  agattttt acctgggtt gctgtaaggg tgcaacatca gggcgcttga gttgctgaga
2041  tgcaaggaat tctataaaata acccattcat agcatagcta gagattggtg aattgaatgc
2101  tcctgacatc tcagttcttg tcagtgaagc tatccaaata actggccaac tagttgttaa
2161  aagctaacag ctcaatctct taaaacactt ttcaaaatat gtgggaagca tttgatttc
2221  aattttgattt tgaattctgc atttggttt atgaataacaa agataagtga aaagagagaa
2281  aggaaaagaa aaaggagaaa aacaaagaga tttctaccag tgaaaggga attaattact
2341  ctttgttagc actcactgac tcttctatgc agttactaca tatctagtaa aaccttgttt
2401  aatactataa ataatattct attcatttg aaaaacacaa tgattccttc ttttctaggc
2461  aatataagga aagtgatcca aaatttgaaa tattaaaata atatctaata aaaagtcaca
2521  aagttatctt cttaacaaa cttactcatt attcttagct gtatatacat ttttttaaaa
2581  agtttgttaa aatatgcttg actagagtt cagttgaaag gcaaaaactt ccatcacaac
2641  aagaaaatttc ccatgcctgc tcagaaggt agcccctagc tctctgtgaa tgtgttttat
2701  ccattcaact gaaaattggt atcaagaaag tccactggtt agtgtactag tccatcatag
2761  cctagaaaat gatccctatc tgcagatcaa gatttctca ttagaacaat gaattatcca
2821  gcattcagat cttctagtc acctagaac tttttggtta aaagtaccca ggcttgatta
2881  tttcatgcaa atctatatt ttacattctt ggaaagtcta tatgaaaac aaaaataaca
2941  tcttcagttt ttctcccact gggtcacctc aaggatcaga ggccaggaaa aaaaaaaaag
3001  actccctgga tctctgaata tatgcaaaaa gaaggcccca tttagttggag ccagcaatcc
3061  tgttcagtca acaagtattt taactctcag tccaacatta tttgaattga gcacctcaag
3121  catgcttagc aatgttctaa tcactatgga cagatgtaaa agaaactata catcattttt
3181  gccctctgcc tgttttccag acatacaggt tctgtggaat aagatactgg actcctcttc
```

FIG. 4B-2

```
3241 ccaagatggc acttcttttt atttcttgtc cccagtgtgt accttttaaa attattccct
3301 ctcaacaaaa ctttataggc agtcttctgc agacttaaca tgttttctgt catagttaga
3361 tgtgataatt ctaagagtgt ctatgactta tttccttcac ttaattctat ccacagtcaa
3421 aaatccccca aggaggaaag ctgaaagatg caactgccaa tattatcttt cttaactttt
3481 tccaacacat aatcctctcc aactggatta taaataaatt gaaaataact cattatacca
3541 attcactatt ttatttttta atgaattaaa actagaaaac aaattgatgc aaacctgga
3601 agtcagttga ttactatata ctacagcaga atgactcaga tttcatagaa aggagcaacc
3661 aaaatgtcac aaccaaaact ttacaagctt tgcttcagaa ttagattgct ttataattct
3721 tgaatgaggc aatttcaaga tatttgtaaa agaacagtaa acattggtaa gaatgagctt
3781 tcaactcata ggcttattc caatttaatt gaccatactg gatacttagg tcaaatttct
3841 gttctctctt gcccaaataa tattaagta ttatttgaac tttttaagat gaggcagttc
3901 ccctgaaaaa gttaatgcag ctctccatca gaatccactc ttctagggat atgaaaatct
3961 cttaacaccc acctacata cacagacaca cacacacaca cacacacaca cacacacaca
4021 cacacattca cctaaggat ccaatggaat actgaaaaga aatcacttcc ttgaaaattt
4081 tattaaaaaa caaacaaaca aacaaaaagc ctgtccaccc ttgagaatcc ttcctctct
4141 tggaacgtca atgtttgtgt agatgaaacc atctcatgct ctgtggctcc agggtttctg
4201 ttactatttt atgcacttgg gagaaggctt agaataaaag atgtagcaca ttttgcttc
4261 ccatttattg tttggccagc tatgccaatg tggtgctatt gttctttaa gaaagtactt
4321 gactaaaaaa aaagagaaaaa aagaaaaaaa agaaagcata gacatatttt tttaaagtat
4381 aaaaacaaca attctataga tagatggctt aataaaatag cattaggtct atctagccac
4441 caccacctt caactttta tcactcacaa gtagtgtact gttcaccaaa ttgtgaattt
4501 gggggtgcag gggcaggagt tggaaatttt ttaaagttag aaggctccat tgttttgttg
4561 gctctcaaac ttagcaaaat tagcaatata ttatccaatc ttctgaactt gatcaagagc
4621 atggagaata aacgcgggaa aaaagatctt ataggcaaat agaagaattt aaaagataag
4681 taagttcctt attgatttt gtgcactctg ctctaaaaca gatattcagc aagtggagaa
4741 aataagaaca aagagaaaaa atacatagat ttacctgcaa aaaatagctt ctgccaaatc
```

FIG. 4B-3

```
4801  cccctgggt attctttggc attactggt ttatagaaga cattctccct tcacccagac
4861  atctcaaaga gcagtagctc tcatgaaaag caatcactga tctcatttgg gaaatgttgg
4921  aaagtattc cttatgagat gggggttatc tactgataaa gaaagaattt atgagaaatt
4981  gttgaaagag atggctaaca atctgtgaag atttttgtt tcttggttt gttttttt
5041  tttttttac tttatacagt ctttatgaat ttcttaatgt tcaaaatgac ttggttcttt
5101  tcttcttttt tttatatcag aatgaggaat aataagttaa acccacatag actctttaaa
5161  actataggct agatagaaat gtatgtttga cttgttgaag ctataatcag actatttaaa
5221  atgttttgct atttttaatc ttaaaagatt gtgctaattt attagagcag aacctgtttg
5281  gctctcctca gaagaaagaa tctttccatt caaatcacat ggctttccac caatatttc
5341  aaaagataaa tctgatttat gcaatggcat catttatttt aaaacagaag aattgtgaaa
5401  gtttatgccc ctcccttgca aagaccataa agtccagatc tggtaggggg gcaacaacaa
5461  aaggaaaatg ttgttgattc ttggttttgg atttgtttt gtttcaatg ctagtgtta
5521  atcctgtagt acatatttgc ttattgctat tttaatattt tataagacct tcctgttagg
5581  tattagaaag tgatacatag atatctttt tgtgtaattt ctatttaaaa aagagagaag
5641  actgtcagaa gctttaagtg catatggtac aggataaaga tatcaattta aataaccaat
5701  tcctatctgg aacaatgctt ttgtttttta aagaaacctc tcacagataa gacagaggcc
5761  caggggattt ttgaagctgt cttattctg ccccatccc aaccccagccc ttattattt
5821  agtatctgcc tcagaatttt atagagggct gaccaagctg aaactctaga attaaaggaa
5881  cctcactgaa aacatatatt tcacgtgttc cctctctttt ttttcctttt tgtgagatgg
5941  ggtctcgcac tgtcccccag gctggagtgc agtggcatga tctcggctca ctgcaacctc
6001  cacctcctgg gtttaagcga ttctcctgcc tcagcctcct gagtagctgg gattacaggc
6061  acccaccact atgcccggct aatttttgg atttttaata gagacgggt tttaccatgt
6121  tggccaggtt ggactcaaac tcctgacctt gtgatttgcc cgcctcagcc tcccaaattg
6181  ctgggattac aggcatgagc caccacacc tgccatgtg ttccctctta atgtatgatt
6241  acatgatct aaacatgat cctctctcc tcattcttca actatctttg atgggtctt
6301  tcaaggggaa aaaaatccaa gcttttttaa agtaaaaaaa aaaaagaga ggacacaaaa
```

FIG. 4B-4

```
6361  ccaaatgtta ctgctcaact gaaatatgag ttaagatgga gacagagttt ctcctaataa
6421  ccggagctga attaccttc actttcaaaa acatgacctt ccacaatcct tagaatctgc
6481  cttttttat attactgagg cctaaaagta aacattactc atttatttt gcccaaaatg
6541  cactgatgta aagtaggaaa aataaaaaca gagctctaaa atcccttca agccaccat
6601  tgaccccact caccaactca tagcaaagtc acttctgtta atcccttaat ctgattttgt
6661  ttggatatatt atctgtgacc cgctgctaaa cacactgcag gagggactct gaaacctcaa
6721  gctgtctact tacatcttt atctgtgtct gtgtatcatg aaaatgtcta ttcaaaatat
6781  caaaacttt caaatatcac gcagcttata ttcagtttac ataaaggccc caaataccat
6841  gtcagatctt tttggtaaaa gagttaatga actatgagaa ttgggattac atcatgtatt
6901  ttgcctcatg tatttttatc acacttatag gccaagtgtg ataaataaac ttacagacac
6961  tgaattaatt tcccctgcta ctttgaaacc agaaaaataat gactggccat tcgttacatc
7021  tgtcttagtt gaaagcata ttttttatta aattaattct gattgtattt gaaattatta
7081  ttcaattcac ttatggcaga ggaatatcaa tcctaatgac ttctaaaaat gtaactaatt
7141  gaatcattat cttacattta ctgtttaata agcatatttt gaaaatgtat ggctagagtg
7201  tcataataaa atggtatatc ttcttagt aattacaaaa aaaaaaaaa aaaaaaaaa (SEQ ID NO:4)
```

FIG. 4B-5

SEQUENCE LISTING

```
<160> NUMBER OF SEQ ID NOS: 4

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60
```

Lys Pro Ala Lys Ser Ala
65                  70

<210> SEQ ID NO 2
<211> LENGTH: 67
<212> TYPE: PRT
<213> ORGANISM: Homo sapiens

<400> SEQUENCE: 2

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 3
<211> LENGTH: 153
<212> TYPE: PRT
<213> ORGANISM: Homo sapiens

<400> SEQUENCE: 3

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 4
<211> LENGTH: 7260
<212> TYPE: DNA
<213> ORGANISM: Homo sapiens

<400> SEQUENCE: 4
tcactgtcac tgctaaattc agagcagatt agagcctgcg caatggaata aagtcctcaa      60
aattgaaatg tgacattgct ctcaacatct cccatctctc tggatttcct tttgcttcat     120
tattcctgct aaccaattca ttttcagact ttgtacttca gaagcaatgg gaaaaatcag     180
cagtcttcca acccaattat ttaagtgctg cttttgtgat tcttgaaggt gaagatgca     240

```
caccatgtcc tcctcgcatc tcttctacct ggcgctgtgc ctgctcacct tcaccagctc      300
tgccacggct ggaccggaga cgctctgcgg ggctgagctg gtggatgctc ttcagttcgt      360
gtgtggagac aggggctttt atttcaacaa gcccacaggg tatggctcca gcagtcggag      420
ggcgcctcag acaggcatcg tggatgagtg ctgcttccgg agctgtgatc taaggaggct      480
ggagatgtat tgcgcacccc tcaagcctgc caagtcagct cgctctgtcc gtgcccagcg      540
ccacaccgac atgcccaaga cccagaagga agtacatttg aagaacgcaa gtagagggag      600
tgcaggaaac aagaactaca ggatgtagga agaccctcct gaggagtgaa gagtgacatg      660
ccaccgcagg atcctttgct ctgcacgagt tacctgttaa actttggaac acctaccaaa      720
aaataagttt gataacattt aaaagatggg cgtttccccc aatgaaatac acaagtaaac      780
attccaacat tgtctttagg agtgatttgc accttgcaaa atggtcctg gagttggtag       840 attgctgttg atcttttatc aataatgttc tatagaaaag aaaaaaaaat atatatatat      900
atatatctta gtccctgcct ctcaagagcc acaaatgcat gggtgttgta tagatccagt      960
tgcactaaat tcctctctga atcttggctg ctggagccat tcattcagca accttgtcta     1020
agtggtttat gaattgtttc cttatttgca cttctttcta cacaactcgg gctgtttgtt     1080
ttacagtgtc tgataatctt gttagtctat acccaccacc tcccttcata acctttatat     1140
ttgccgaatt tggcctcctc aaaagcagca gcaagtcgtc aagaagcaca ccaattctaa     1200
cccacaagat tccatctgtg gcatttgtac caaatataag ttggatgcat tttattttag     1260
acacaaagct ttatttttcc acatcatgct tacaaaaaag aataatgcaa atagttgcaa     1320 cttttgaggcc aatcattttt aggcatatgt tttaaacata gaaagtttct tcaactcaaa    1380
agagttcctt caaatgatga gttaatgtgc aacctaatta gtaactttcc tcttttatt      1440 ttttccatat agagcactat gtaaatttag catatcaatt atacaggata tatcaaacag     1500
tatgtaaaac tctgtttttt agtataatgg tgctattttg tagtttgtta tatgaaagag     1560
tctggccaaa acggtaatac gtgaaagcaa acaataggg gaagcctgga gccaaagatg      1620
acacaagggg aagggtactg aaaacaccat ccatttggga agaaggcaa agtcccccca      1680 gttatgcctt ccaagaggaa cttcagacac aaaagtccac tgatgcaaat tggactggcg     1740
agtccagaga ggaaactgtg gaatggaaaa agcagaaggc taggaatttt agcagtcctg     1800
gtttcttttt ctcatggaag aaatgaacat ctgccagctg tgtcatggac tcaccactgt     1860
gtgaccttgg gcaagtcact tcacctctct gtgcctcagt ttcctcatct gcaaaatggg     1920
ggcaatatgt catctaccta cctcaaaggg gtggtataag gttaaaaag ataaagattc      1980 agatttttttt accctgggtt gctgtaaggg tgcaacatca gggcgcttga gttgctgaga    2040
tgcaaggaat tctataaata acccattcat agcatagcta gagattggtg aattgaatgc     2100
tcctgacatc tcagttcttg tcagtgaagc tatccaaata actggccaac tagttgttaa     2160
aagctaacag ctcaatctct taaaacactt ttcaaaatat gtgggaagca tttgattttc     2220
aatttgattt tgaattctgc atttggtttt atgaatacaa agataagtga aaagagagaa     2280
aggaaaagaa aaaggagaaa aacaaagaga tttctaccag tgaaagggga attaattact     2340
ctttgttagc actcactgac tcttctatgc agttactaca tatctagtaa aaccttgttt     2400
aatactataa ataatattct attcatttg aaaacacaa tgattccttc ttttctaggc       2460
aatataagga aagtgatcca aaatttgaaa tattaaaata atatctaata aaaagtcaca     2520
aagttatctt ctttaacaaa ctttactctt attcttagct gtatatacat ttttttaaaa    2580
agtttgttaa aatatgcttg actagagttt cagttgaaag gcaaaaactt ccatcacaac     2640
```

```
aagaaatttc ccatgcctgc tcagaagggt agccctagc tctctgtgaa tgtgttttat      2700
ccattcaact gaaaattggt atcaagaaag tccactggtt agtgtactag tccatcatag      2760
cctagaaaat gatccctatc tgcagatcaa gattttctca ttagaacaat gaattatcca      2820
gcattcagat ctttctagtc acctagaaac ttttttggtta aaagtaccca ggcttgatta     2880
tttcatgcaa attctatatt ttacattctt ggaaagtcta tatgaaaaac aaaaataaca      2940
tcttcagttt ttctcccact gggtcacctc aaggatcaga ggccaggaaa aaaaaaaag      3000 actccctgga tctctgaata tatgcaaaaa gaaggcccca tttagtggag ccagcaatcc     3060
tgttcagtca acaagtattt taactctcag tccaacatta tttgaattga gcacctcaag     3120
catgcttagc aatgttctaa tcactatgga cagatgtaaa agaaactata catcattttt     3180
gccctctgcc tgttttccag acatacaggt tctgtggaat aagatactgg actcctcttc     3240
ccaagatggc acttcttttt atttcttgtc cccagtgtgt accttttaaa attattccct     3300
ctcaacaaaa ctttataggc agtcttctgc agacttaaca tgttttctgt catagttaga     3360
tgtgataatt ctaagagtgt ctatgactta tttccttcac ttaattctat ccacagtcaa     3420
aaatccccca aggaggaaag ctgaaagatg caactgccaa tattatcttt cttaactttt     3480
tccaacacat aatcctctcc aactggatta taaataaatt gaaataaact cattatacca     3540
attcactatt ttatttttta atgaattaaa actagaaaac aaattgatgc aaaccctgga     3600
agtcagttga ttactatata ctacagcaga atgactcaga tttcatagaa aggagcaacc     3660
aaaatgtcac aaccaaaact ttacaagctt tgcttcagaa ttagattgct ttataattct     3720
tgaatgaggc aatttcaaga tatttgtaaa agaacagtaa acattggtaa gaatgagctt     3780
tcaactcata ggcttatttc caatttaatt gaccatactg gatacttagg tcaaatttct     3840
gttctctctt gcccaaataa tattaaagta ttatttgaac tttttaagat gaggcagttc     3900
ccctgaaaaa gttaatgcag ctctccatca gaatccactc ttctagggat atgaaaatct     3960
cttaacaccc accctacata cacagacaca cacacacaca cacacacaca cacacacaca     4020
cacacattca ccctaaggat ccaatggaat actgaaaaga aatcacttcc ttgaaaattt     4080
tattaaaaaa caaacaaaca aacaaaaagc ctgtccaccc ttgagaatcc ttcctctcct     4140
tggaacgtca atgtttgtgt agatgaaacc atctcatgct ctgtggctcc agggtttctg     4200
ttactatttt atgcacttgg gagaaggctt agaataaaag atgtagcaca ttttgctttc     4260
ccatttattg tttggccagc tatgccaatg tggtgctatt gtttctttaa gaaagtactt     4320
gactaaaaaa aaaagaaaaa aagaaaaaaa agaaagcata gacatatttt tttaaagtat     4380
aaaaacaaca attctataga tagatggctt aataaaatag cattaggtct atctagccac     4440 caccacccttt caactttta tcactcacaa gtagtgtact gttcaccaaa ttgtgaattt      4500
gggggtgcag gggcaggagt tggaaatttt ttaaagttag aaggctccat tgttttgttg     4560
gctctcaaac ttagcaaaat tagcaatata ttatccaatc ttctgaactt gatcaagagc     4620
atggagaata aacgcgggaa aaaagatctt ataggcaaat agaagaattt aaaagataag     4680
taagttcctt attgattttt gtgcactctg ctctaaaaca gatattcagc aagtggagaa     4740
aataagaaca aagagaaaaa atacatagat ttacctgcaa aaaatagctt ctgccaaatc     4800
cccctttggg attctttggc atttactggt ttatagaaga cattctcccct tcacccagac    4860 atctcaaaga gcagtagctc tcatgaaaag caatcactga tctcatttgg gaaatgttgg     4920
aaagtatttc cttatgagat gggggttatc tactgataaa gaaagaattt atgagaaatt     4980
gttgaaagag atggctaaca atctgtgaag attttttgtt tcttggtttt gttttttttt     5040
```

```
tttttttttac tttatacagt ctttatgaat ttcttaatgt tcaaaatgac ttggttctttt    5100
tcttctttttt tttatatcag aatgaggaat aataagttaa acccacatag actctttaaa    5160
actataggct agatagaaat gtatgtttga cttgttgaag ctataatcag actatttaaa    5220
atgttttgct atttttaatc ttaaaagatt gtgctaattt attagagcag aacctgtttg    5280
gctctcctca gaagaaagaa tctttccatt caaatcacat ggctttccac caatatttc    5340
aaaagataaa tctgatttat gcaatggcat catttatttt aaaacagaag aattgtgaaa    5400
gtttatgccc ctcccttgca aagaccataa agtccagatc tggtaggggg gcaacaacaa    5460
aaggaaaatg ttgttgattc ttggttttgg attttgtttt gttttcaatg ctagtgttta    5520
atcctgtagt acatatttgc ttattgctat tttaatattt tataagacct tcctgttagg    5580
tattagaaag tgatacatag atatctttt tgtgtaattt ctatttaaaa aagagagaag    5640
actgtcagaa gctttaagtg catatggtac aggataaaga tatcaattta aataaccaat    5700
tcctatctgg aacaatgctt ttgttttta aagaaacctc tcacagataa gacagaggcc    5760
caggggattt ttgaagctgt ctttattctg ccccatccc aacccagccc ttattatttt    5820
agtatctgcc tcagaatttt atagagggct gaccaagctg aaactctaga attaaaggaa    5880
cctcactgaa aacatatatt tcacgtgttc cctctcttt ttttcctttt tgtgagatgg    5940
ggtctcgcac tgtcccccag gctggagtgc agtggcatga tctcggctca ctgcaacctc    6000
cacctcctgg gtttaagcga ttctcctgcc tcagcctcct gagtagctgg gattacaggc    6060
acccaccact atgcccggct aatttttttgg attttaata gagacggggt tttaccatgt    6120
tggccaggtt ggactcaaac tcctgacctt gtgatttgcc cgcctcagcc tcccaaattg    6180
ctgggattac aggcatgagc caccacaccc tgcccatgtg ttccctctta atgtatgatt    6240
acatggatct taaacatgat cctctctcc tcattcttca actatctttg atgggggtctt    6300
tcaaggggaa aaaaatccaa gcttttttaa agtaaaaaaa aaaaagaga ggacacaaaa    6360
ccaaatgtta ctgctcaact gaaatatgag ttaagatgga gacagagttt ctcctaataa    6420
ccggagctga attaccttc actttcaaaa acatgacctt ccacaatcct tagaatctgc    6480
cttttttat attactgagg cctaaaagta aacattactc attttattt gcccaaaatg    6540
cactgatgta aagtaggaaa aataaaaaca gagctctaaa atccctttca agccacccat    6600
tgaccccact caccaactca tagcaaagtc acttctgtta atcccttaat ctgattttgt    6660
ttggatattt atcttgtacc cgctgctaaa cacactgcag gagggactct gaaacctcaa    6720
gctgtctact tacatctttt atctgtgtct gtgtatcatg aaaatgtcta ttcaaaatat    6780
caaaaccttt caaatatcac gcagcttata ttcagtttac ataaaggccc caaataccat    6840
gtcagatctt tttggtaaaa gagttaatga actatgagaa ttgggattac atcatgtatt    6900
ttgcctcatg tatttttatc acacttatag gccaagtgtg ataaataaac ttacagacac    6960
tgaattaatt tcccctgcta ctttgaaacc agaaaataat gactggccat tcgttacatc    7020
tgtcttagtt gaaaagcata ttttttatta aattaattct gattgtatt gaaattatta    7080
ttcaattcac ttatggcaga ggaatatcaa tcctaatgac ttctaaaaat gtaactaatt    7140
gaatcattat cttacattta ctgtttaata agcatatttt gaaaatgtat ggctagagtg    7200
tcataataaa atggtatatc tttctttagt aattacaaaa aaaaaaaaa aaaaaaaaa    7260
```

METHODS AND COMPOSITIONS FOR TARGETING PROTEINS ACROSS THE BLOOD BRAIN BARRIER

RELATED APPLICATIONS

This application is a continuation of U.S. patent application Ser. No. 11/234,876, filed Sep. 23, 2005, which is a continuation of U.S. patent application Ser. No. 10/136,639, filed Apr. 30, 2002, which claims the benefit of U.S. Ser. No. 60/329,650, filed Oct. 16, 2001, the entire disclosures of all of which are incorporated by reference.

FIELD OF THE INVENTION

This invention provides a means for specifically delivering proteins to the brain. The ability to target proteins to the brain is of great utility in the treatment of neurological diseases. Methods and compositions of the invention are useful to target proteins to cells across the blood brain barrier, and in particular, to target proteins to the lysosomes of cells in the CNS, including neuronal cells, macrophage cells, and other cell types. Accordingly, the invention provides methods and compositions to deliver therapeutically useful proteins to treat lysosomal storage diseases that affect the CNS.

BACKGROUND

The blood-brain barrier maintains a homeostatic environment in the central nervous system (CNS). The capillaries that supply the blood to the brain have tight junctions which block passage of most molecules through the capillary endothelial membranes. While the membranes do allow passage of lipid soluble materials, water soluble materials such as glucose, proteins and amino acids do not pass through the blood brain barrier. Mediated transport mechanisms exist to transport glucose and essential amino acids across the blood brain barrier. Active transport mechanisms remove molecules which become in excess, such as potassium, from the brain. However, the blood brain barrier impedes the delivery of drugs to the CNS.

Many neurological diseases result from cellular defects in the CNS. In particular, many lysosomal storage diseases affect cells of the CNS and result in mild to serious neurological symptoms. Accordingly, the ability to deliver therapeutic compositions to the CNS is an important aspect of an effective treatment for many diseases, including many lysosomal storage diseases.

Methods have been designed to deliver needed drugs to the CNS such as direct delivery within the CNS by intrathecal delivery. However, methods are not available in the art to efficiently deliver drugs, and particularly protein-based drugs, from the blood stream to the CNS through the blood brain barrier.

Therefore, there is a need in the art for methods to deliver proteins to the brain parenchyma on the CNS side of the blood brain barrier, and in particular to deliver proteins to the lysosomes of cells in the CNS.

SUMMARY OF THE INVENTION

The present invention provides general methods and compositions for targeting compositions from the blood stream to the brain or CNS. According to the invention, an IGF moiety is used to target a molecule from the blood stream to the brain parenchyma on the other side of the blood brain barrier. Preferred molecules are therapeutic polypeptides.

Accordingly, the invention relates in one aspect to a protein including a therapeutic agent attached to an insulin-like growth factor (IGF) moiety or tag. In one embodiment, the protein is expressed as a fusion protein along with the IGF tag. In a preferred embodiment, the fusion protein also includes a lysosomal targeting portion sufficiently duplicative of IGF-II such that the targeting portion binds the cation independent mannose-6-phosphate/IGF-II receptor to mediate uptake by a lysosome. In another embodiment, the fusion protein also comprises mannose-6-phosphate in order to target the protein to the lysosomes.

Preferred IGF moieties or tags are IGF-I or IGF-II tags. Most preferred IGF tags are IGF-I tags. In one aspect, the IGF tag is an intact IGF-I or IGF-II protein. Alternatively, an IGF tag is a portion of an IGF-I or IGF-II protein that is sufficient for targeting through the blood brain barrier. Preferred portions comprise at least one of the A, B, C, or D domains, or the C-terminal region or a portion thereof, of either IGF-I or IGF-II. In one embodiment, an IGF tag includes both an A and a B domain. According to the invention, the A and B domains provide core structural features of a preferred IGF moiety. The A and B domains may be linked by a linker peptide. Alternatively, the A and B domains may be provided as separate peptides that dimerize to form an IGF tag. Preferably, A and B domains from the same IGF protein are used. However, an A domain from IGF-I can be associated with a B domain from IGF-II. Similarly, an A domain from IGF-II can be associated with a B domain from IGF-I. Accordingly, composition of the invention include chimeric IGF-I/IGF-II molecules. For example, an A domain from one IGF protein can be joined to the C and B domains of another IGF protein. Alternative combinations of A, B, and C domains are also useful. In further embodiments, the A domain of one IGF protein can be joined directly to the domain of another IGF protein, for example by using an amino acid bridge such as a two amino acid bridge.

A most preferred IGF moiety comprises an IGF-I portion selected from the group consisting of IGF-I fragments from about residue 1 to about residue 25, IGF-I fragments from about residue 25 to about residue 40, IGF-I fragments from about residue 40 to about residue 65, and IGF-I fragments from about residue 65 to about residue 70 of the IGF-I sequence shown in FIG. 1. Alternative preferred regions of IGF-I and IGF-II comprise regions of homology between IGF-I and IGF-II such as those shown in FIG. 1 for human IGF-I and IGF-II. The sequences shown in FIG. 1 relate to mature IGF-I and IGF-II proteins. Specific IGF variants described herein refer to the mature amino acid sequence numbering shown in FIG. 1. In a further embodiment, an IGF tag comprises the C-terminal fragment of an IGF protein, for example the region C-terminal to the D domain shown in FIG. 2. A preferred IGF tag includes an IGF-I C-terminal fragment. In addition, according to the invention, IGF tags include peptide tags with a sequence that is sufficiently duplicative of the IGF tags described herein to effectively target compositions of the invention to the brain parenchyma across the blood brain barrier. In some embodiments, an IGF tag includes at least one peptide sequence from an IGF-I protein and one from an IGF-II protein.

Most preferred IGF tags are based on human IGF proteins. However, IGF tags based on IGF proteins from other mammals, such as mouse, rabbit, monkey, and pig IGF proteins, are also useful according to the invention. Preferred IGF tags such as the IGF fragments, peptides, or domains described herein are between 1 and 100 amino acids long, more preferably between 10 and 50 amino acids long, and even more preferably about 25 amino acids long, and are sufficient for targeting associated peptides to the brain. Preferred IGF fragments, peptides, or domains are based on the mature IGF-I and IGF-II sequences.

IGF tags of the invention can be fused to a therapeutic peptide at its N-terminus, C-terminus, within the body of the therapeutic peptide, or a combination of the above. When an IGF moiety is fused to the N-terminus of a therapeutic protein, an IGF signal peptide is preferably included in the expression construct. However, an IGF signal peptide can also be included at the N-terminus when the IGF targeting moiety is located at the C-terminus or within the body of the therapeutic protein. In a preferred embodiment, the IGF tag is fused to the C-terminal end of a peptide. In one embodiment, a first domain of an IGF tag is fused to a therapeutic peptide, and a second domain of the IGF tag is provided in a form that dimerizes with the first domain resulting in a protein that is targeted to the brain. For example, the therapeutic peptide can be fused to the A domain of an IGF protein, and dimerized with a B domain that is provided separately. Alternatively, the therapeutic peptide can be fused to the B domain of an IGF protein, and dimerized with an A domain that is provided separately.

The invention also relates to methods for identifying IGF-based peptide fragments that can reach neuronal tissue from blood and are useful to target an associated protein to the brain or CNS. According to the invention, the effectiveness of IGF-based tags can be assayed using methods described herein, such as localization assays based on radioactive labels or histochemical staining.

The invention also relates to a nucleic acid encoding an IGF tag or a protein fused to an IGF tag, and to a cell (e.g., a cell cultured in vitro including a mammalian cell culture such as a CHO cell culture, and/or a unicellular organism such as *E. coli* or *Leishmania*) containing such a nucleic acid.

In another aspect, the invention relates to a method of producing a therapeutic agent for targeting across the blood brain barrier, and in particular to the lysosomes of cells in the CNS. The agent is produced by culturing a cell expressing a nucleic acid encoding a protein containing both a therapeutic agent and an IGF tag effective to target the protein across the blood brain barrier. The protein is then harvested (e.g. from the milieu about the cell, or by lysing the cell). The invention also relates to protein compositions described herein.

The invention also relates to methods of treating a patient (e.g. a patient with a disorder in the CNS, and preferably a CNS disorder resulting from a lysosomal storage disorder) by administering, for example, a protein including a therapeutic agent effective in the mammalian CNS and an IGF tag to target the protein to the CNS. Preferably, the protein also comprises a lysosomal targeting portion such as those described in entitled "Methods and Compositions for Lysosomal Targeting" filed on Apr. 30, 2002, or mannose-6-phosphate to target the protein to the lysosomes of deficient cells in the CNS. Similarly, the invention relates to methods of treating a patient by administering a nucleic acid encoding such a protein and/or by administering a cell (e.g. a human cell, or an organism such as *Leishmania*) containing a nucleic acid encoding such a protein.

BRIEF DESCRIPTION OF THE DRAWINGS

FIG. 4 shows protein (FIG. 4A)(SEQ ID NO:3) and nucleic acid (FIG. 4B)(SEQ ID NO:4) sequences for human IGF-I mRNA.

DETAILED DESCRIPTION OF THE INVENTION

CNS Targeting Portion

Figure 1:
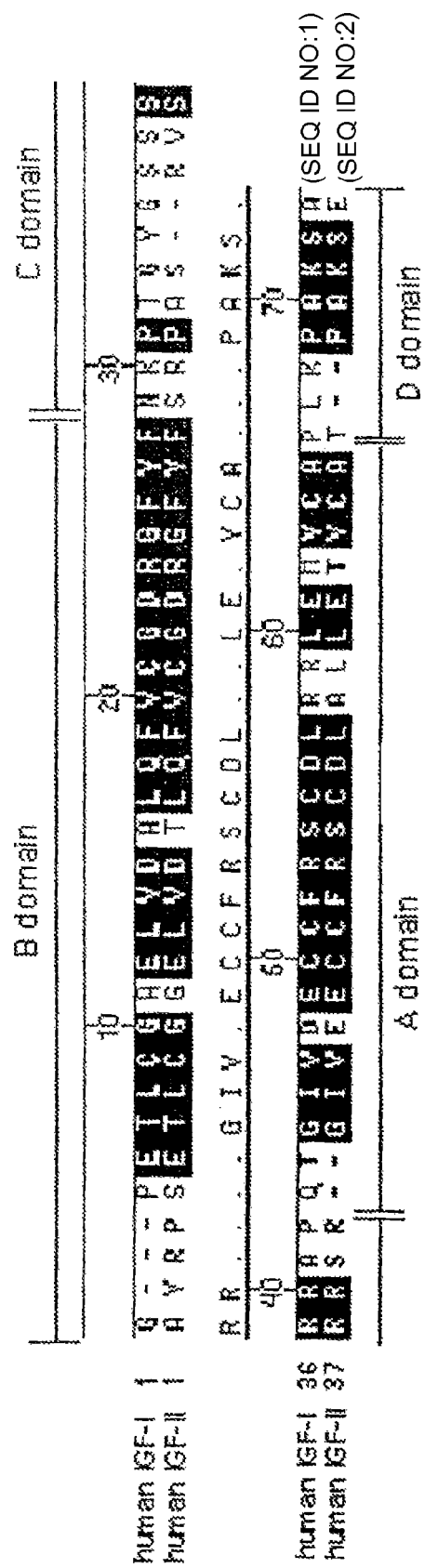
FIG. 1 shows a sequence alignment of mature human IGF-I (SEQ ID NO:1) and IGF-II (SEQ ID NO:2), indicating regions of homology and the A, B, C, and D domains.

According to the invention, an IGF moiety is useful for targeting a composition, preferably a protein composition, to the CNS, across the blood brain barrier. Preferably, an IGF tag is used to target a composition to the brain parenchyma. According to the invention, a composition may enter the CNS or brain parenchyma either directly across the blood-brain barrier (the BBB) or indirectly across the blood-cerebrospinal fluid barrier (the BCB). The BBB is formed by capillary endothelial cells and the BCB is formed by epithelial cells of the choroid plexus. Transport across either barrier typically involves transcytosis. According to the invention, a composition that is targeted across the BCB to the CSF can subsequently reach the brain parenchyma. The CSF and brain parenchyma are separated by the ependyma, and diffusion or bulk flow can transport substances between these two compartments.

The invention exploits, in part, the recognition that [125I]-IGF-I and IGF-II can be detected in the brain when infused into the carotid artery, and that IGF-I and analogs administered subcutaneously can be found in the cerebrospinal fluid. According to the invention, this suggests that both can traverse the BBB or BCB. According to the invention, the observed saturation of the transport process suggests that the process is carrier mediated. However, experimental analysis using a series of IGF-I analogs suggests that the IGF-I receptor, the IGF-II receptor, and IGF binding proteins-1,-3,-4, or 5 do not play a role in the blood brain barrier transport.

According to one aspect of the invention, preferred therapeutic compositions include a therapeutic peptide fused to an IGF tag. Preferred therapeutic composition include IGF-I tags that will direct LSD (lysosomal storage disease) proteins to which they are fused across the blood brain barrier. In this instance, the tag will not necessarily direct the protein to the lysosome of multiple cell types. However, by expressing such fusion proteins in mammalian cell culture systems, the invention exploits the endogenous M6P signal for lysosomal localization and uses the IGF-I tag to traverse the blood brain barrier. In preferred embodiments of the invention, a human IGF-I tag is used. In alternative embodiments, methods and compositions of the invention involve using allelic, species or other sequence variants of an IGF-I tag. Preferred sequence variants include mutations that lessen binding of the IGF tag to the IGF-I receptor and/or IGF binding proteins such as a substitution of leucine at a position corresponding to $Tyr^{60}$ of IGF-I, or a substitution of leucine at a position corresponding to $Tyr^{24}$ of IGF-I which have diminished binding to the IGF-I receptor or Δ1-3 IGF-I which has diminished binding to IGF-binding proteins. Additional useful sequence variants include IGF-I variants with amino acid replacements of $Arg^{55}$ and $Arg^{56}$. Other mutant IGF protein tags with similar properties are also useful.

IGF-II based tags are also useful to target proteins to the brain. IGF-II has been reported to be transported across the blood brain barrier via transcytosis (Bickel et al. (2001) Adv. Drug Deliv. Rev. 46(1-3):247-79). According to the invention, preferred IGF-II-based tags target proteins to the brain and also target proteins to the lysosome via receptor binding in order to treat neurological symptoms associated with lysosomal storage diseases. Preferred variants of IGF-II have an amino acid replacement of leucine at a position corresponding to Tyr$^{24}$.

In another aspect of the invention, chimeric tags are used that include fragments of IGF-I and IGF-II, conferring preferred functional properties of each protein. In one embodiment, the retained portion of IGF-II includes regions of IGF-II known to be critical for binding to the IGF-II M6P receptor while the remainder of IGF-II would be substituted for the corresponding regions of IGF-I. This embodiment, is particularly useful where IGF-I is more active as a tag for traversing the blood brain barrier. In this embodiment, the tag has optimized activity for lysosomal targeting in addition to brain targeting. A recombinant form of this embodiment could be made in any expression system.

In a further aspect of the invention, a useful recombinant LSD protein includes any one of the different IGF-based lysosomal targeting tags described in entitled "Methods and Compositions for Lysosomal Targeting" filed on Apr. 30, 2002.

In preferred embodiments, recombinant proteins of the invention including IGF-II tags are expressed in a mammalian expression system such as a CHO cell expression system. According to the invention, the endogenous M6P signal added in the mammalian cell culture enhances the lysosomal targeting that may be provided by an IGF-II tag.

According to the invention, useful minimal IGF tags and variant IGF tags can be identified based on known IGF-I and IGF-II sequences by testing minimal or variant IGF fragments in a CNS localization assay such as one described herein.

A preferred IGF tag is sufficiently duplicative of IGF-I to be targeted to the brain, but has reduced binding affinity for the IGF-I receptor thereby removing the mitogenic properties of IGF-I. However, a preferred IGF tag does bind to the IGF-II receptor in order to be targeted to lysosomes. Accordingly, in one embodiment, an IGF tag is based on the IGF-I sequence but includes two hydrophobic IGF-II residues at positions 54 and 55 instead of the IGF-I Arg residues at these positions.

Structure of IGF-II

NMR structures of IGF-II have been solved by two groups (see, e.g., Protein Data Bank record 1IGL). The general features of the IGF-II structure are similar to IGF-I and insulin. The A and B domains of IGF-II correspond to the A and B chains of insulin. Secondary structural features include an alpha helix from residues 11-21 of the B region connected by a reverse turn in residues 22-25 to a short beta strand in residues 26-28. Residues 25-27 appear to form a small antiparallel beta sheet; residues 59-61 and residues 26-28 may also participate in intermolecular beta-sheet formation. In the A domain of IGF-II, alpha helices spanning residues 42-49 and 53-59 are arranged in an antiparallel configuration perpendicular to the B-domain helix. Hydrophobic clusters formed by two of the three disulfide bridges and conserved hydrophobic residues stabilize these secondary structure features. The N and C termini remain poorly defined as is the region between residues 31-40.

IGF-II binds to the IGF-II/M6P and IGF-I receptors with relatively high affinity and binds with lower affinity to the insulin receptor. IGF-II also interacts with a number if serum IGFBPs.

Binding to the IGF-II/M6P Receptor

Substitution of IGF-II residues 48-50 (Phe Arg Ser) with the corresponding residues from insulin, (Thr Ser Ile), or substitution of residues 54-55 (Ala Leu) with the corresponding residues from IGF-I (Arg Arg) result in loss of binding to the IGF-II/M6P receptor but retention of binding to the IGF-I and insulin receptors.

IGF-I and IGF-II share identical sequences and structures in the region of residues 48-50 yet have a 1000-fold difference in affinity for the IGF-II receptor. The NMR structure reveals a structural difference between IGF-I and IGF-H in the region of IGF-II residues 53-58 (IGF-I residues 54-59): the alpha-helix is better defined in IGF-II than in IGF-I and, unlike IGF-I, there is no bend in the backbone around residues 53 and 54. This structural difference correlates with the substitution of Ala 54 and Leu 55 in IGF-II with Arg 55 and Arg 56 in IGF-I. It is possible either that binding to the IGF-II receptor is disrupted directly by the presence of charged residues in this region or that changes in the structure engendered by the charged residues yield the changes in binding for the IGF-II receptor. In any case, substitution of uncharged residues for the two Arg residues in IGF-I resulted in higher affinities for the IGF-II receptor. Thus the presence of positively charged residues in these positions correlates with loss of binding to the IGF-II receptor.

IGF-II binds to repeat 11 of the cation-independent M6P receptor. Indeed, a minireceptor in which only repeat 11 is fused to the transmembrane and cytoplasmic domains of the cation-independent M6P receptor is capable of binding IGF-II (with an affinity approximately one tenth the affinity of the full length receptor) and mediating internalization of IGF-II and its delivery to lysosomes (Grimme et al. (2000) *J. Biol. Chem.* 275(43):33697-33703). The structure of domain II of the M6P receptor is known (Protein Data Base entries 1GP0 and 1GP3; Brown et al. (2002) *EMBO J.* 21(5):1054-1062). The putative IGF-II binding site is a hydrophobic pocket believed to interact with hydrophobic amino acids of IGF-II; candidate amino acids of IGF-II include leucine 8, phenylalanine 48, alanine 54, and leucine 55. Although repeat 11 is sufficient for IGF-II binding; constructs including larger portions of the cation-independent M6P receptor (e.g. repeats 10-13, or 1-15) generally bind IGF-II with greater affinity and with increased pH dependence (see, for example, Linnell et al. (2001) *J. Biol. Chem.* 276(26):23986-23991).

Binding to the IGF-I Receptor

Substitution of IGF-II residues Tyr 27 with Leu, Leu 43 with Val or Ser 26 with Phe diminishes the affinity of IGF-II for the IGF-I receptor by 94-, 56-, and 4-fold respectively. Deletion of residues 1-7 of human IGF-II resulted in a 30-fold decrease in affinity for the human IGF-I receptor and a concomitant 12 fold increase in affinity for the rat IGF-II receptor. The NMR structure of IGF-II shows that Thr 7 is located near residues 48 Phe and 50 Ser as well as near the 9 Cys-47 Cys disulfide bridge. It is thought that interaction of Thr 7 with these residues can stabilize the flexible N-terminal hexapeptide required for IGF-I receptor binding. At the same time this interaction can modulate binding to the IGF-II receptor. Truncation of the C-terminus of IGF-II (residues 62-67) also appear to lower the affinity of IGF-II for the IGF-I receptor by 5 fold.

Deletion Mutants of IGF-II

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids 1-7 and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) *Trends Biochem. Sci.* 279-281). Thus, for example, amino acids 8-28, or a conservative substitution variant thereof, could be fused to a therapeutic agent; the resulting fusion protein could be admixed with amino acids 41-61, or a conservative substitution variant thereof, and administered to a patient.

Binding to IGF Binding Proteins

IGF-II and related constructs can be modified to diminish their affinity for IGFBPs, thereby increasing the bioavailability of the tagged proteins.

Substitution of IGF-II residue phenylalanine 26 with serine reduces binding to IGFBPs 1-5 by 5-75 fold. Replacement of IGF-II residues 48-50 with threonine-serine-isoleucine reduces binding by more than 100 fold to most of the IGFBPs; these residues are, however, also important for binding to the cation-independent mannose-6-phosphate receptor. The Y27L substitution that disrupts binding to the IGF-I receptor interferes with formation of the ternary complex with IGFBP3 and acid labile subunit; this ternary complex accounts for most of the IGF-II in the circulation. Deletion of the first six residues of IGF-II also interferes with IGFBP binding.

Studies on IGF-I interaction with IGFBPs revealed additionally that substitution of serine for phenylalanine 16 did not effect secondary structure but decreased. IGFBP binding by between 40 and 300 fold. Changing glutamate 9 to lysine also resulted in a significant decrease in IGFBP binding. Furthermore, the double mutant lysine 9/serine 16 exhibited the lowest affinity for IGFBPs. Although these mutations have not previously been tested in IGF-II, the conservation of sequence between this region of IGF-I and IGF-II suggests that a similar effect will be observed when the analogous mutations are made in IGF-II (glutamate 12 lysine/phenylalanine 19 serine).

IGF Homologs

The amino acid sequence of human IGF-I, IGF-II, or a portion thereof affecting transport into the brain, may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to human IGF-I or IGF-II.

Figure 2:
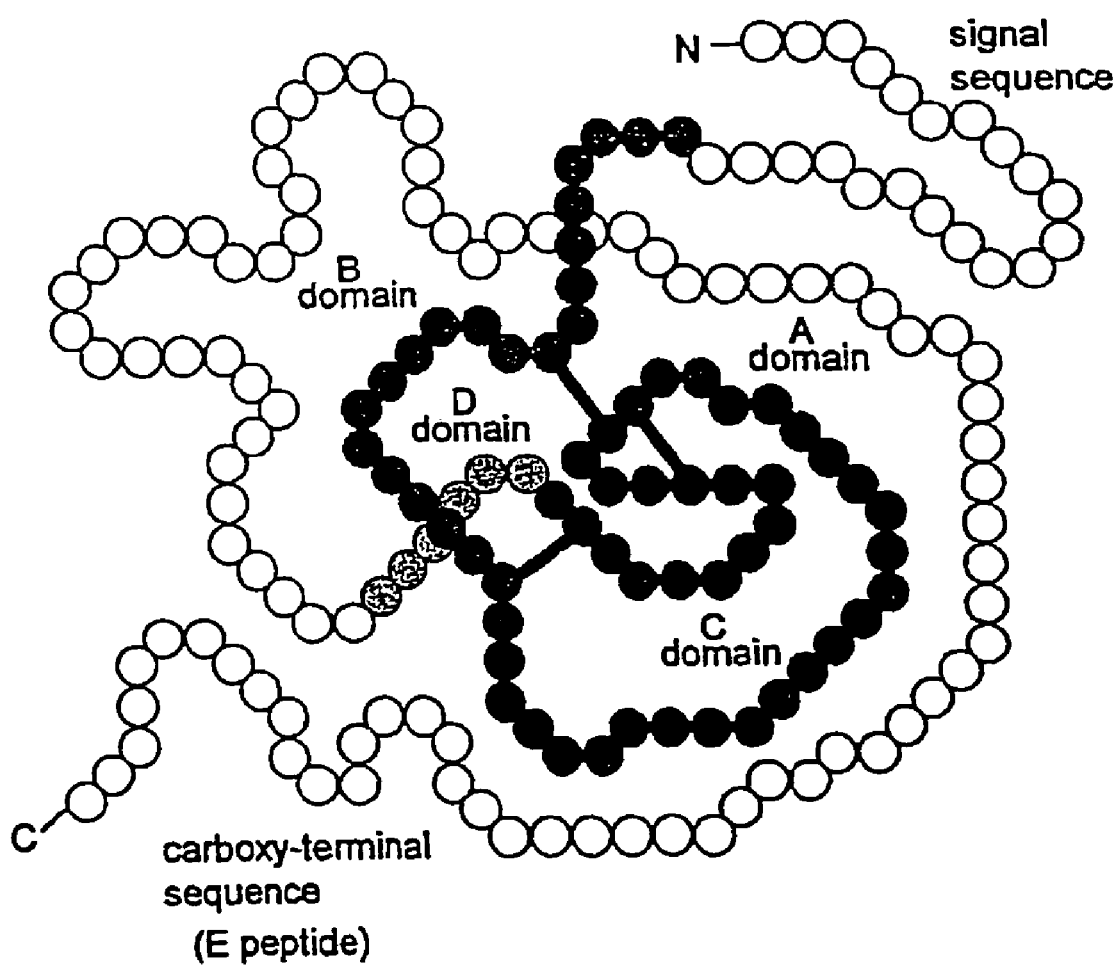
FIG. 2 is a two-dimensional representation of an IGF protein showing the signal sequence, the A, B, C, and D domains, and the C terminal sequence.
Figure 3:
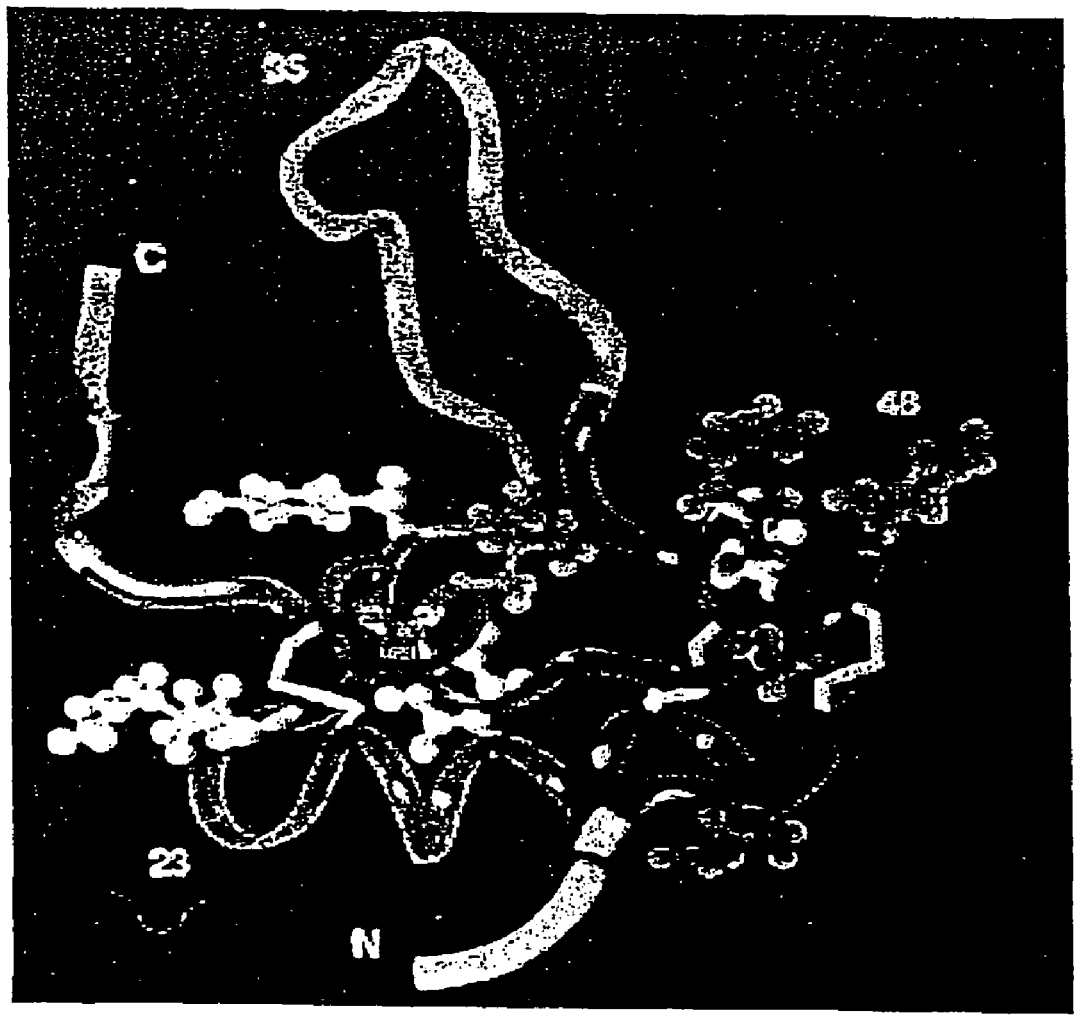
FIG. 3 is a depiction the 3 dimensional structure of an IGF protein.

To determine whether a candidate peptide region has the requisite percentage similarity or identity to human IGF-I or IGF-II, the candidate amino acid sequence and human IGF-I or IGF-II are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *PNAS* 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

IGF Structural Analogs

The known structures of human IGF proteins permit the design of IGF analogs using computer-assisted design principles such as those discussed in U.S. Pat. Nos. 6,226,603 and 6,273,598. For example, the known atomic coordinates of IGF-II can be provided to a computer equipped with a conventional computer modeling program, such as INSIGHTII, DISCOVER, or DELPHI, commercially available from Biosym, Technologies Inc., or QUANTA, or CHARMM, commercially available from Molecular Simulations, Inc. These and other software programs allow analysis of molecular structures and simulations that predict the effect of molecular changes on structure and on intermolecular interactions. For example, the software can be used to identify modified analogs with the ability to form additional intermolecular hydrogen or ionic bonds, improving the affinity of the analog for the target receptor.

The software also permits the design of peptides and organic molecules with structural and chemical features that mimic the same features displayed on at least part of an IGF surface that is sufficient for targeting to the CNS. A preferred embodiment of the present invention relates to designing and producing a synthetic organic molecule having a framework that carries chemically interactive moieties in a spatial relationship that mimics the spatial relationship of the chemical moieties disposed on the amino acid sidechains which are identified as associated with CNS targeting as described herein.

For example, upon identification of relevant chemical groups, the skilled artisan using a conventional computer program can design a small molecule having appropriate chemical moieties disposed upon a suitable carrier framework. Useful computer programs are described in, for example, Dixon (1992) Tibtech 10: 357-363; Tschinke et al. (1993) *J. Med. Chem* 36: 3863-3870; and Eisen et al. (1994) *Proteins: Structure, Function, and Genetics* 19: 199-221, the disclosures of which are incorporated herein by reference.

One particular computer program entitled "CAVEAT" searches a database, for example, the Cambridge Structural Database, for structures which have desired spatial orientations of chemical moieties (Bartlett et al. (1989) in "Molecular Recognition: Chemical and Biological Problems" (Roberts, S. M., ed) pp 182-196). The CAVEAT program has been used to design analogs of tendamistat, a 74 residue inhibitor of .alpha.-amylase, based on the orientation of selected amino acid side chains in the three-dimensional structure of tendamistat (Bartlett et al. (1989) supra).

Alternatively, upon identification of a series of analogs which target transport to the CNS, the skilled artisan may use a variety of computer programs which assist the skilled artisan to develop quantitative structure activity relationships (QSAR) and further to assist in the de novo design of additional analogs. Other useful computer programs are described in, for example, Connolly-Martin (1991) Methods in Enzymology 203:587-613; Dixon (1992) supra; and Waszkowycz et al. (1994) J. Med. Chem. 37: 3994-4002.

Therapeutic Agent

While methods and compositions of the invention are useful for producing and delivering any therapeutic agent to the CNS, the invention is particularly useful for gene products that overcome enzymatic defects associated with lysosomal storage diseases.

Preferred LSD genes are shown in Table 1. In a preferred embodiment, a wild-type LSD gene product is delivered to a patient suffering from a defect in the same LSD gene. In alternative embodiments, a functional sequence or species variant of the LSD gene is used. In further embodiments, a gene coding for a different enzyme that can rescue an LSD gene defect is used according to methods of the invention.

TABLE 1

Lysosomal Storage Diseases and associated enzyme defects

| Disease Name | Enzyme Defect | Substance Stored |
|---|---|---|
| A. Glycogenosis Disorders | | |
| Pompe Disease | Acid-a1,4-Glucosidase | Glycogen α 1-4 linked Oligosaccharides |
| B. Glycolipidosis Disorders | | |
| GM1 Gangliodsidosis | β-Galactosidase | GM$_1$ Ganliosides |
| Tay-Sachs Disease | β-Hexosaminidase A | GM$_2$ Ganglioside |
| GM2 Gangliosidosis: AB Variant | GM$_2$ Activator Protein | GM$_2$ Ganglioside |
| Sandhoff Disease | β-Hexosaminidase A&B | GM$_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A and B | Acid Sphingomyelinase | Sphingomyelin |
| Niemann-Pick, Type C | Cholesterol Esterification Defect | Sphingomyelin |
| Nieman-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Asparylglucosaminuria | N-Aspartyl-β-Glucosaminidase | Asparylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders | | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other | | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In one embodiment, the therapeutic agent is glucocerebrosidase, currently manufactured by Genzyme as an effective enzyme replacement therapy for Gaucher Disease. Currently, the enzyme is prepared with exposed mannose residues, which targets the protein specifically to cells of the macrophage lineage. Although the primary pathology in type 1 Gaucher patients are due to macrophage accumulating glucocerebroside, there may be therapeutic advantage to delivering glucocerebrosidase to other cell types. Targeting glucocerebrosidase to lysosomes using the present invention would target the agent to multiple cell types and may have a therapeutic advantage compared to other preparations.

Association Between Targeting Portion and Therapeutic Portion

The therapeutic portion and the targeting portion of compositions of the invention are necessarily associated, directly or indirectly. In one embodiment, the therapeutic portion and the targeting portion are non-covalently associated. For example, the targeting portion could be biotinylated and bind an avidin moiety associated with the therapeutic portion. Alternatively, the targeting portion and the therapeutic portion could each be associated (e.g. as fusion proteins) with different subunits of a multimeric protein. In another embodiment, the targeting portion and the therapeutic portion are crosslinked to each other (e.g. using a chemical crosslinking agent).

In a preferred embodiment, the therapeutic portion is fused to the targeting portion as a fusion protein. The targeting portion may be at the amino-terminus of the fusion protein, the carboxy-terminus, or may be inserted within the sequence of the therapeutic portion at a position where the presence of the targeting portion does not unduly interfere with the therapeutic activity of the therapeutic portion.

Where the therapeutically active moiety is a heteromeric protein, one or more of the subunits may be associated with a targeting portion. Hexosaminidase A, for example, a lysosomal protein affected in Tay-Sachs disease, includes an alpha subunit and a beta subunit. Either the alpha subunit, or the beta subunit, or both may be associated with a targeting portion in accordance with the present invention. If, for example, the alpha subunit is associated with a targeting portion and is coexpressed with the beta subunit, an active complex is formed and targeted to the lysosome.

Methods

Methods and compositions of the invention are useful in the context of many different expression systems. For example, a protein of the invention can be targeted to the CNS, and preferably taken up by lysosomes, whether it is expressed and isolated from *Leishmania*, baculovirus, yeast or bacteria. Thus, the invention permits great flexibility in protein production. For example, if a protein to be produced includes one or more disulfide bonds, an appropriate expression system can be selected and modified, if appropriate, to further improve yield of properly folded protein. For example, one useful IGF targeting portion has three intramolecular disulfide bonds. Fusion proteins of the invention expressed in *E. coli* may be constructed to direct the protein to the periplasmic space. IGF tags, when fused to the C-terminus of another protein, can be secreted in an active form in the periplasm of *E. coli* (Wadensten, Ekebacke et al. 1991). To facilitate optimal folding of the IGF moiety, appropriate concentrations of reduced and oxidized glutathione are preferably added to the cellular milieu to promote disulfide bond formation. In the event that a fusion protein with disulfide bonds is incompletely soluble, any insoluble material is preferably treated with a chaotropic agent such as urea to solubilize denatured protein and refolded in a buffer having appropriate concentrations of reduced and oxidized glutathione, or other oxidizing and reducing agents, to facilitate formation of appropriate disulfide bonds (Smith, Cook et al. 1989). For example, IGF-I has been refolded using 6M guanidine-HCl and 0.1 M tris(2-carboxyethyl)phosphine reducing agent for denaturation and reduction of IGF-II (Yang, Wu et al. 1999). Refolding of proteins was accomplished in 0.1M Tris-HCl buffer (pH8.7) containing 1 mM oxidized glutathione, 10 mM reduced glutathione, 0.2M KCl and 1 mM EDTA.

Methods of the invention are also useful to target a protein directly to the CNS of a mammal without requiring a purification step. In one embodiment, an IGF fusion protein is expressed in a symbiotic or parasitic organism that is administered to a host. The expressed IGF fusion protein is secreted by the organism into the blood stream and delivered across the blood brain barrier.

In some embodiments of the invention, CNS targeted proteins are delivered in situ via live *Leishmania* secreting the proteins into the lysosomes of infected macrophage. From this organelle, it leaves the cell and may be delivered across the blood brain barrier. Thus, the IGF tag and the therapeutic agent necessarily remain intact while the protein resides in the macrophage lysosome. Accordingly, when proteins designed for delivery to lysosomes in the CNS are expressed in situ, they are preferably modified to ensure compatibility with the lysosomal environment. In alternative embodiments, therapeutic proteins of the invention can be delivered by expression in *T. brucei* which can penetrate the BCB.

EXAMPLES

Example 1

Fusion Protein Expressing Constructs

Nucleic acid constructs for expressing therapeutic protein fusions of the invention can be made recombinantly according to methods known in the art. For example, oligonucleotides complementary to genes encoding the different components described herein can be used to make synthetic genes or to amplify the natural genes and construct gene fusions. In preferred embodiments, proteins of the invention are expressed from a recombinant gene comprising a signal sequence. Examples of useful nucleic acids include nucleic acids that encode IGF targeting moieties of the invention. Such nucleic acids can be based on the sequences of IGF-1 shown in FIG. 4.

Example 2

Expression and Purification Methods

Expression product can also be isolated from serum free media using other protozoa, including other *Leishmania* species. In general, the expression strain is grown in medium with serum, diluted into serum free medium, and allowed to grow for several generations, preferably 2-5 generations, before the expression product is isolated. For example, production of secreted recombinant LSD proteins can be isolated from *Leishmania mexicana* promastigotes that are cultured initially in 50 mL 1×M199 medium in a 75 cm2 flask at 27° C. When the cell density reaches $1\text{-}3\times10^7$/mL, the culture is used to inoculate 1.2 L of M199 media. When the density of this culture reaches about $5\times10^6$/mL, the cells were harvested by centrifugation, resuspended in 180 mL of the supernatant and used to inoculate 12 L of "Zima" medium in a 16 L spinner flask. The initial cell density of this culture is typically about $5\times10^5$/mL. This culture is expanded to a cell density of about $1.0\text{-}1.7\times10e^7$ cells/mL. When this cell density is reached, the cells are separated from the culture medium by centrifugation and the supernatant is filtered at 4° C. through a 0.2μ filter to remove residual promastigotes. The filtered media was concentrated from 12.0 L to 500 mL using a tangential flow filtration device (MILLIPORE Prep/Scale-TFF cartridge).

Preferred growth media for this method are M199 and "Zima" growth media. However, other serum containing and serum free media are also useful. M199 growth media is as follows: (1 L batch)=200 mL 5×M199 (with phenol pH indicator) mixed at 5×+637 mL H$_2$O, 50.0 mL FBS, 50.0 mL EF, 20.0 mL of 50 g/mL SAT, 2.0 mL of 0.25% hemin in 50% triethanolamine, 10 mL of 10 mM adenine in 50 mM Hepes pH 7.5, 40.0 mL of 1M Hepes pH 7.5, 1 mL of 0.1% biotin in 95% ethanol, 10.0 mL of penicillin/streptomycin. All serums used are inactivated by heat. The final volume 1 L and is filter sterilized. "Zima" modified M199 media is as follows: (20.0 L batch) 217.8 g M199 powder (−)phenol red+7.0 g sodium bicarbonate, 200.0 mL of 10 mM adenine in 50 mM Hepes pH 7.5, 800.0 µL of Hepes free acid pH 7.5, 20.0 mL 0.1% biotin in 95% ethanol, 200.0 mL penicillin/streptomycin, 2780.0 mL H$_2$0 Final volume=20.0 L and is filter sterilized.

According to one aspect of the invention, LSD proteins secreted from *Leishmania* and containing carbohydrate with terminal mannose residues can be purified as follows. For example, recombinant β-glucuronidase from *Leishmania mexicana* containing plasmsid pXSAP0-GUS was grown in M199 culture medium with a small amount of serum proteins. When the culture reached a density of >1.0×10$^7$ promastigotes/mL the *L. mexicana* were removed by centrifugation, 10 min at 500×g. The harvested culture medium was passed through a 0.2 µm filter to remove particulates before being loaded directly onto a Concanavalin A (ConA)-agarose column (4% cross-linked beaded agarose, Sigma). The ConA-agarose column was pretreated with 1 M NaCl, 20 mM Tris pH 7.4, 5 mM each of CaCl$_2$, MgCl$_2$ and MnCl$_2$ and then equilibrated with 5 volumes of column buffer (20 mM Tris pH 7.4, 1 mM CaCl$_2$, and 1 mM MnCl$_2$). A total of 179,800 units (nmol/hr) of GUS activity (in 2 L) in culture medium was loaded onto a 22 mL ConA agarose column. No activity was detectable in the flow through or wash. The GUS activity was eluted with column buffer containing 200 mM methyl mannopyranoside. Eluted fractions containing the activity peak were pooled and concentrated: 143900 units of GUS activity were recovered from the column (80% recovery of activity loaded onto the column). This demonstrates that the recombinant β-GUS secreted from *L. mexicana* possesses carbohydrate with terminal mannose residues and further points out the potential for using the interaction of mannose with ConA as the basis for an affinity purification step. Accordingly, the presence of high mannose carbohydrate can serve as the basis of an affinity step in the purification of recombinant LSD proteins using lectin affinity chromatography.

Example 3

Assays for Crossing the Blood Brain Barrier

According to the invention, a useful model system to determine whether a protein, particularly an LSD protein, tagged with an IGF tag crosses the blood-brain barrier, is the MPSVII mouse model (Wolfe and Sands (1996) *Protocols for Gene Transfer in Neuroscience: Towards Gene Therapy of Neurological Disorders* Chapter 20: 263-273). For example, recombinant human β-glucuronidase fused to an IGF tag can be produced in any convenient expression system such as *Leishmania*, yeast, mammalian, bacculovirus and other expression systems. *L. mexicana* expressing and secreting β-GUS is grown at 26° C. in 100 ml Standard Promastigote medium (M199 with 40 mM HEPES, pH 7.5, 0.1 mM adenine, 0.0005% hemin, 0.0001% biotin, 5% fetal bovine serum, 5% embryonic fluid, 50 units/ml penicillin, 50 μg/ml streptomycin and 50 μg/ml nourseothricin). After reaching a density of approximately 5×10^6 promastigotes/ml, the promastigotes is collected by centrifugation for 10 min. at 1000×g at room temperature; these promastigotes were used to inoculate 1 liter of low protein medium (M199 supplemented with 0.1 mM adenine, 0.0001% biotin, 50 units/ml penicillin and 50 μg/ml streptomycin) at room temperature. The 1 liter cultures are contained in 2 liter capped flasks with a sterile stir bar so that the cultures could be incubated at 26° C. with gentle stirring. The 1 liter cultures are aerated twice a day by moving them into a laminar flow hood, removing the caps and swirling vigorously before replacing the caps. When the cultures reach a density of 2-3×10^7 promastigotes/ml, the cultures are centrifuged as previously described except the promastigote pellet is discarded and the media decanted into sterile flasks. The addition of 434 g $(NH_4)_2SO_4$ per liter precipitates active GUS protein from the medium; the salted out medium is stored at 4° C. overnight. Precipitated proteins are harvested either by centrifugation at 10,500×g for 30 min. or filtration through Gelman Supor-800 membrane; the proteins are resuspended in 10 mM Tris pH 8, 1 mM $CaCl_2$ and stored at −80° C. until dialysis. The crude preparations from several liters of medium are thawed, pooled, placed in dialysis tubing (Spectra/Por-7, MWCO 25,000), and dialyzed overnight against two 1 liter volumes of DMEM with bicarbonate (Dulbecco's Modified Eagle's Medium). The ammonium sulfate fraction is further purified on a ConA column.

GUS minus mice generated by heterozygous matings of B6.C—H-$2^{bml}$/ByBIR-$gus^{mps}$/+ mice are used to assess the effectiveness of GUS-IGF fusion proteins or derivatives in enzyme replacement therapy. Two formats are used. In one format, 3-4 animals are given a single injection of 20,000 U of enzyme in 100 μl enzyme dilution buffer (150 mM NaCl, 10 mM Tris, pH7.5). Mice are killed 72-96 hours later to assess the efficacy of the therapy. In a second format, mice are given weekly injections of 20,000 units over 3-4 weeks and are killed 1 week after the final injection. Histochemical and histopathologic analysis of liver, spleen and brain are carried out by published methods. In the absence of therapy, cells (e.g. macrophages and Kupffer cells) of GUS minus mice develop large intracellular storage compartments resulting from the buildup of waste products in the lysosomes. It is anticipated that in cells in mice treated with GUS fusion constructs of the invention, the size of these compartments will be visibly reduced or the compartments will shrink until they are no longer visible with a light microscope.

According to the invention, newborn mice do not possess a complete blood brain barrier. However, by day 15 the blood brain barrier is formed to the point that β-glucuronidase no longer can be detected in the brain. Accordingly, the above experiments are preferably performed on mice that are at day 15 or greater.

According to one embodiment of the invention, experiments first assess the ability of complete IGF-I and IGF-II tags to direct proteins across the blood brain barrier. Next, specific mutant versions of the proteins that disrupt receptor or IGF binding protein binding are assayed. For domain swaps, the B domain of IGF-II (residues 1-28 of the mature protein) contains only two differences from IGF-I that could conceivably alter transport across the blood brain barrier G11 and T16. Altering these residues in IGF-II would is essentially a domain B swap. Another swap of regions between residues 28 and 41 of IGF-II and the corresponding region of IGF-I can also be tested. This essentially swaps the C domains of the two proteins which contains the most divergent regions of the two proteins. An alternative swap switches the C-terminal 15 residues with the corresponding region of IGF-I. These three chimeras provide an essentially complete picture of how any differences in uptake across the blood brain barrier between IGF-I and IGF-II correlate with sequence/structural differences between the two proteins.

Example 4

Assays for Protein Accumulation in the Brain or CNS

Radioactive assays can be used to monitor the accumulation of protein product in the brain. For example, the uptake and accumulation of a radioactively labeled protein in the brain parenchyma can be assayed as disclosed in Reinhardt and Bondy (1994) *Endocrinology* 135:1753-1761.

Enzyme assays can also be used to monitor the accumulation of protein product in the brain. Enzyme assays are particularly useful when the therapeutic protein moiety is an enzyme for which there is an assay that is applicable for histochemical staining. Useful enzyme assays for lysosomal storage disease proteins include assays disclosed in Sly at al. (2001) *P.N.A.S.* 98(5): 2205-2210, and in Wolfe and Sands (1996) *Protocols for Gene Transfer in Neuroscience: Towards Gene Therapy of Neurological Disorders* Chapter 20: 263-273.

Example 5

In Vivo Therapy

GUS minus mice generated by heterozygous matings of B6.C—H-2$^{bm1}$/ByBIR-gus$^{mps}$/+ mice (Birkenmeier, Davisson et al. 1989) are used to assess the effectiveness of compositions of the invention in enzyme replacement therapy. Two formats are used. In one format, 3-4 animals are given a single injection of 20,000 U of enzyme in 100 µl enzyme dilution buffer (150 mM NaCl, 10 mM Tris, pH7.5). Mice are killed 72-96 hours later to assess the efficacy of the therapy. In a second format, mice are given weekly injections of 20,000 units over 3-4 weeks and are killed 1 week after the final injection. Histochemical and histopathologic analysis of liver, spleen and brain are carried out by published methods (Birkenmeier, Barker et al. 1991; Sands, Vogler et al. 1994; Daly, Vogler et al. 1999). In the absence of therapy, cells (e.g. macrophages and Kupffer cells) of GUS minus mice develop large intracellular storage compartments resulting from the buildup of waste products in the lysosomes. It is anticipated that in cells in mice treated with compositions of the invention, the size of these compartments will be visibly reduced or the compartments will shrink until they are no longer visible with a light microscope.

Similarly, humans with lysosomal storage diseases will be treated using constructs targeting an appropriate therapeutic portion to their CNS and in particular to lysosomes within the CNS. In some instances, treatment will take the form of regular (e.g. weekly) injections of a fusion protein of the invention. In other instances, treatment will be achieved through administration of a nucleic acid to permit persistent in vivo expression of the fusion protein, or through administration of a cell (e.g. a human cell, or a unicellular organism) expressing the fusion protein in the patient. For example, a protein the invention may be expressed in situ using a *Leishmania* vector as described in U.S. Pat. No. 6,020,144, issued Feb. 1, 2000; and PCT Serial No. PCT/US01/44935, filed Nov. 30, 2001.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The disclosure of each of the patent documents and scientific publications disclosed herein, and U.S. Ser. No. 60/250,446 filed Nov. 30, 2000; U.S. Ser. No. 60/250,444 filed Nov. 30, 2000; U.S. Ser. No. 60/290,281 filed May 11, 2001; U.S. Ser. No. 60/287,531, filed Apr. 30, 2001; U.S. Ser. No. 60/304,609, filed Jul. 10, 2001; U.S. Ser. No. 60/329,461, filed Oct. 15, 2001, a U.S. Ser. No. 60/351,276, filed Jan. 23, 2002; and entitled "Methods and Compositions for Lysosomal Targeting" filed on Apr. 30, 2002; PCT Serial No. PCT/US01/44935, filed Nov. 30, 2001; are incorporated by reference into this application in their entirety.

---

The invention claimed is:

1. A targeted therapeutic fusion protein comprising: a lysosomal enzyme; and a mutein of human IGF-I having an amino acid sequence at least 80% identical to mature human IGF-I (SEQ ID NO:1); wherein the mutein of IGF-I comprises an amino acid substitution selected from the group consisting of leucine at a position corresponding to Tyr$^{60}$, leucine at a position corresponding to Tyr$^{24}$, serine at a position corresponding to Phe$^{16}$, and lysine at a position corresponding to Glu$^9$, or amino acid substitutions at positions corresponding to Arg$^{55}$ and Arg$^{56}$, of mature human IGF-I (SEQ ID NO:1); and wherein the mutein binds to the human cation-independent mannose-6-phosphate receptor in a mannose-6-phosphate-independent manner.

2. The targeted therapeutic fusion protein of claim 1, wherein the mutein of human IGF-I comprises an amino acid substitution of leucine at a position corresponding to Tyr$^{60}$ of mature human IGF-I (SEQ ID NO:1).

3. The targeted therapeutic fusion protein of claim 1, wherein the mutein of human IGF-I comprises an amino acid substitution of leucine at a position corresponding to Tyr$^{24}$ of mature human IGF-I (SEQ ID NO:1).

4. The targeted therapeutic fusion protein of claim 1, wherein the mutein of human IGF-I comprises an amino acid substitution of serine at a position corresponding to Phe$^{16}$ of mature human IGF-I (SEQ ID NO:1).

5. The targeted therapeutic fusion protein of claim 1, wherein the mutein of human IGF-I comprises an amino acid substitution of lysine at a position corresponding to Glu$^9$ of mature human IGF-I (SEQ ID NO:1).

6. The targeted therapeutic fusion protein of claim 1, wherein the mutein of human IGF-I comprises amino acid substitutions at positions corresponding to Arg$^{55}$ and Arg$^{56}$ of mature human IGF-I (SEQ ID NO:1).

7. A targeted therapeutic fusion protein comprising: a lysosomal enzyme; and a mutein of human IGF-I having an amino acid sequence at least 80% identical to mature human IGF-I (SEQ ID NO:1); wherein the mutein binds to the human cation-independent mannose-6-phoshate receptor in a mannose-6-phoshate-independent manner and wherein the fusion protein is deglycosylated.

8. The targeted therapeutic fusion protein of claim 6, wherein the fusion protein is deglycosylated by periodate treatment.

\* \* \* \* \*